(12) United States Patent
Popa et al.

(10) Patent No.: US 8,815,539 B1
(45) Date of Patent: Aug. 26, 2014

(54) METHODS FOR PRODUCING MELANIN AND INORGANIC FERTILIZER FROM FERMENTATION LEACHATES

(71) Applicant: River Road Research, Inc., Tonawanda, NY (US)

(72) Inventors: Radu Popa, Los Angeles, CA (US); Kenneth H. Nealson, South Pasadena, CA (US)

(73) Assignee: River Road Research, Inc., Tonawanda, NY (US)

( * ) Notice: Subject to any disclaimer, the term of this patent is extended or adjusted under 35 U.S.C. 154(b) by 0 days.

(21) Appl. No.: 13/911,927

(22) Filed: Jun. 6, 2013

(51) Int. Cl.
C12P 39/00 (2006.01)

(52) U.S. Cl.
USPC ............... 435/42; 435/41; 530/300; 530/317

(58) Field of Classification Search
None
See application file for complete search history.

(56) References Cited

U.S. PATENT DOCUMENTS

| 2012/0187041 A1 | 7/2012 | Popa et al. |
| 2014/0020630 A1 | 1/2014 | Courtright |

OTHER PUBLICATIONS

Alattar, Manar Arica, "Biological Treatment of Leachates of Microaerobic Fermentation" (2012). Dissertations and Theses (Open Access). Paper 905. http://dr.archives.pdx.edu/xmlui/handle/psu/7959.*

Nappi, Cellular immunity and pathogen strategies in combative interactions involving Drosophila hosts and their endoparasitic wasps, 2010, ISJ 7: 198-210.*

Li, Liposomes Can Specifically Target Entrapped Melanin to Hair Follicles in Histocultured Skin, 1993, In Vitro Cellular & Developmental Biology—Animal 29(3): 192-194.*

Alattar, M.A. et al., "Effect of Microaerobic Fermentation in Preprocessing Fibrous Lignocellulosic Materials," 2012 Appl. Biochem. Biotechnol., vol. 167 (pp. 909-917).

Green, T.R. et al., "Endpoint Fragmentation Index: A Method for Monitoring the Evolution of Microbial Degradation of Polysaccharide Feedstocks," 2011 Appl. Biochem. Biotechnol., vol. 163 (pp. 519-527).

Green, T.R. et al., "Turnover of Carbohydrate-Rich Vegetal Matter During Microaerobic Composting and After Amendment in Soil," 2011 Appl. Biochem. Biotechnol., vol. 165 (pp. 270-278).

Green, T.R. et al., "Enhanced Ammonia Content in Compost Leachate Processed by Black Soldier Fly Larvae," 2012 Appl. Biochem. Biotechnol., vol. 166 (pp. 1381-1387).

Popa R. et al., "Using Black Soldier Fly Larvae for Processing Organic Leachates," 2012 J. Econ. Entomol., vol. 105, No. 2 (pp. 374-378).

(Continued)

*Primary Examiner* — Lora E Barnhart Driscoll
*Assistant Examiner* — Stephanie McNeil
(74) *Attorney, Agent, or Firm* — Harris Beach PLLC

(57) ABSTRACT

Melanin or inorganic fertilizers are produced from fermentation leachates or from low-cost nutrient-rich solutions. The method for producing the melanin or inorganic fertilizer comprises repetitive trophic cycling in the controlled conditions of primary and secondary bioreactors. Nutrients are cycled between microorganisms such as bacteria, yeast and fungi and black soldier fly larvae, *Hermetia illucens*. Polysaccharides are partly converted into natural melanins or inorganic fertilizer, which are difficult to biodegrade and hence accumulate in the bioreactors. The method can employ, as a source of nutrients, leachates produced from food waste or from sugar-rich liquid waste of the food industry. These leachates can be used raw or can be augmented with low-cost sugar-rich solutions such as molasses, hydrolyzed cellulose or starch. The method is inexpensive and does not require the use of expensive chemically-defined culture media.

23 Claims, 5 Drawing Sheets

(56) References Cited

OTHER PUBLICATIONS

Figure 1:
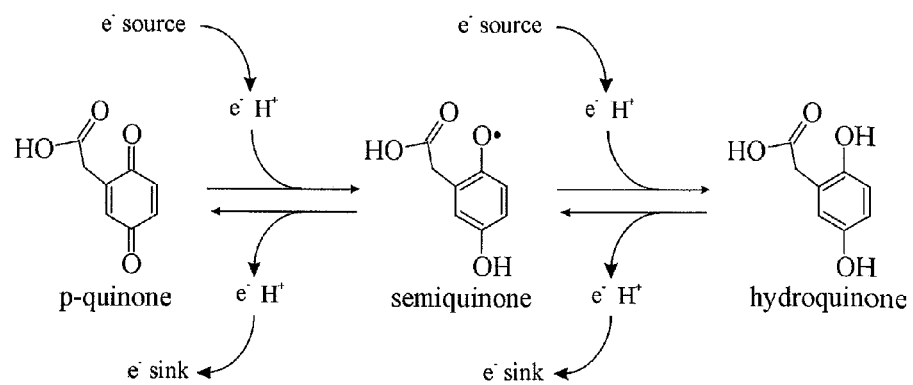

Tomberlin, J.K. et al., "Development of the Black Soldier Fly (Diptera: Stratiomyidae) in Relation to Temperature," 2009 Environ. Entomol., vol. 38, No. 3 (pp. 930-934).

Yabuuchi, E. et al., "Characterization of 'Pyomelanin'-Producing Strains of *Pseudomonas aeruginosa*," Apr. 1972 International Journal of Systematic Bacteriology, vol. 22, No. 2, (pp. 53-64).

* cited by examiner

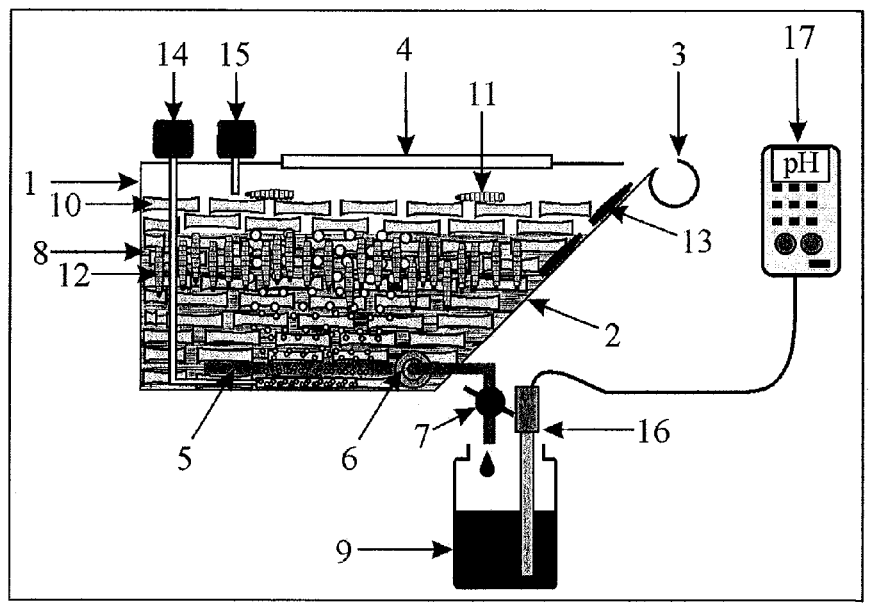
FIG. 6
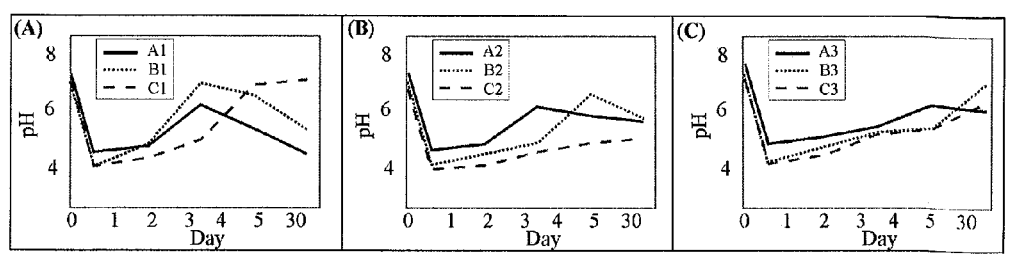
FIGS. 7A-C

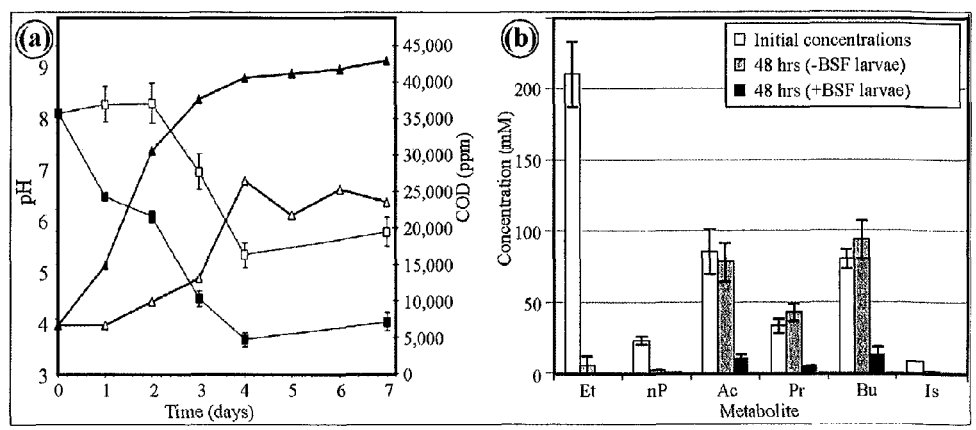
FIGS. 8a-b

METHODS FOR PRODUCING MELANIN AND INORGANIC FERTILIZER FROM FERMENTATION LEACHATES

1. TECHNICAL FIELD

The present invention relates to methods for producing melanin, melanin-associated proteins and inorganic fertilizer from fermentation leachates or from nutrient rich solutions spiked with low cost, sugar-rich sources.

2. BACKGROUND OF THE INVENTION

Melanin is one of a very few examples of natural organic semiconductors and was demonstrated to be such in the early 1970s. Melanin is thus a desirable natural, environmentally friendly material with many known applications for the electronics industry. Melanin can be used to produce a wide variety of biologically friendly electronic devices and batteries used in applications such as medical sensors and tissue stimulation treatments.

Many metazoans and microorganisms form melanin naturally. Because the concentration of melanin in these organisms is generally low and melanin is very insoluble, melanin extraction is inefficient and natural melanin is expensive. It is known in the art that the yield of melanin in a microbial culture can be increased by using chemically defined culture media, targeted extraction from natural populations, culturing pure strains, mutation and selection, genetic modification, and by spiking culture media with melanin precursors such as tyrosine and phenylalanine.

Melanins (such as eumelanin, pheomelanin and pyomelanin) are natural polyphenols produced by living cells. Pyomelanin is a negatively charged hydrophobic polymer of imprecise structure and size (Turick et al., 2003, 2009). It is present in fungi (Nosanchuk and Casadevall, 1997; Carreira et al., 2001; Schmaler-Ripcke et al., 2009), but also in many bacteria such as species of *Pseudomonas* (Yabuuchi and Ohyama, 1972; Arai, 1980), *Legionella* (Chatfield and Cianciotto, 2007) and *Shewanella* (Turick et al., 2008). Unlike the well-known eumalanin, which is produced from dihydroxyphenylalanine (DOPA), pyomelanin is metabolically derived from homogentisic acid (HGA), which upon elimination from cells autooxidizes and polymerizes as pyomelanin (David et al. 1996; Chatfield and Cianciotto 2007; Schmaler-Ripcke, 2009; Yabuuchi and Ohyama, 1972; Ruzafa et al., 1994; Kotob et al., 1995). In cells, pyomelanin is often associated with proteins (albeit melanin associated proteins are relatively little studied), and it is more concentrated in the outer cell envelopes such as the lipopolysaccharide layer and cell capsule (Turick et al., 2003).

The primary role of pyomelanin in living cells remains debated as melanins were proposed to play various roles in different species. Melanins can alter the electrical charge of a cell, especially when the polysaccharide capsule is small or absent (Nosanchuk and Casadevall, 1997). In *Cryptococcus* spp. the expression of pyomelanin is correlated with virulence (Kwon-Chung, 1982). In *Legionella*, pyomelanin increases resistance to light (Steinert et al., 1995). An antioxidant role for pyomelanin has been often proposed and has been demonstrated in *Burkholderia* sp. (Boles et al., 2004; Boles and Singh, 2008) and *Methylococcus thermophilus* (Sokolov et al., 1992). Pyomelanin confers *Legionella* ferric reductase capabilities (Chatfield and Cianciotto, 2007) and may help cells reduce, immobilize or chelate metals (Chatfield and Cianciotto, 2007; Turick et al., 2008; Nyhus et al., 1997). Pyomelanin may also bind and help recycle soluble electron shuttles such as riboflavin or may be used to transfer electrons toward solid phases (Marsili et al., 2008; Turick et al., 2009). The capacity of melanins to transfer electrons is derived from their ability to change the state of their monomers between quinone, semiquinone and hydroquinone (FIG. 1) (McGinness et al., 1974; Turrick et al., 2010). Because melanins have broad energy absorbing properties, their capacity to exchange electrons are influenced by many types of energy sources, including ionizing radiation, UV light, visible light, IR light and heat (Dadachova et al., 2007). It was proposed that in nature pyomelanin may also serve as a terminal electron acceptor (Turick et al., 2008), electron shuttle (Arai et al., 1980; Keith et al., 2007), or conduit for electrons (Turick et al., 2010).

Due to the complex architecture and broad size range of melanin the chemical entourage of the various quinone centers vary within a melanin polymer. Hence, their redox properties also vary, albeit they can exchange electrons within and between melanin polymers. For this reason, rather than having a narrow redox potential ($E_o$) as most simple redox chemicals do, melanin shows a broad redox potential profile. The discharge or recharge of electrons from some quinone centers is likely followed by re-partition of electrons and protons within the polymer until equilibrium is reached. Because most redox transformations involving melanin in nature occur at low redox potential ($dE°<2$ V), the variation in the energy level associated with electron exchanges is small relative to the strength of the covalent bonds which hold the quinone structure together. Henceforth, it can be predicted that as long as charging potentials remain small (say $\leq 2$ V) melanins can be charged:discharged with electrons numerous times without significant alteration of the basic structure. A set of usage conditions can be found (with regard to redox potential and depth of charging/discharging) where the extreme electron-load phases of melanin (i.e. quinone and hydroquionone) are sufficiently stable to allow a melanin based battery to be fully charged or discharged without significant effects on the melanin' stability. Based on these properties, melanins can be used to replace heavy metals as electron storage substrates in the construction of long life, deep cycle rechargeable batteries. Energy storage in melanin is ecofriendly because melanin is composed only of elements (i.e. carbon, oxygen and hydrogen) that are abundant and easily recycled in near earth surface ecosystems. Henceforth, an economy using melanin-based energy storage will not become resource limited, nor will it compete with materials needed by other economic activities.

Relative to other types of melanin, pyomelanin has the benefit of being produced in microbial cultures, has narrow range molecular size, 12,000-14,000 MW (Turrick et al., 2002), and it is easier to dissolve and purify. These properties make pyomelanin an excellent choice for applied technologies that require predictable product quality and predictable redox chemistry. In contrast, eumelanin and pheomelanin are only available in low supply and eumelanin is highly variable in size (it may have a molecular mass as large as $10^6$ g/mol, making some eumelanin fractions highly insoluble). Last but not least, the cost of producing melanin is important in evaluating its sustainability for energy storage devices. Commercial eumelanin is extracted from hair and squid or polymerized from DOPA-related monomers and presently costs between $300 and $600 per gram, which makes it unsuitable for most economical applications. In contrast, pyomelanin extracted from microbial cultures can be produced in large amounts and at considerably lower costs.

Pyomelanin and pyomelanin-related molecules can be produced in various ways. Most frequently proposed methods are: direct extraction from microbial biomass, enrichment in culture media spiked with tyrosine or phenylalanine, induction of genetically modified microorganisms and chemical oxidation of homogentisate. Microorganisms may produce between 1 and 115 fg of pyomelanin per cell (though a 1-10 fg yield is more common) depending on strain and physiological state (Turick et al., 2003; Turick et al., 2008; Turick et al., 2002). Most cell cultures will produce approximately 0.03-0.3% pyomelanin relative to dry weight (DW). Obtaining higher melanin yields requires using pure cultures, inducing agents, long incubation times, expensive media and controlled growth conditions. The biomass obtained in bacterial cultures may vary between 0.23 g DW/L in batch media without manipulated conditions, and 37.8 g DW/L in rich media under controlled conditions (Soini et al., 2008). Hence, simple batch cultures may produce 0.069-0.69 mg pyomelanin $L^{-1}$, while complex controlled cultures may produce as much as 1.13 g pyomelanin $L^{-1}$ (albeit obtaining such extremely high yields is costly).

Citation or identification of any reference in Section 2, or in any other section of this application, shall not be considered an admission that such reference is available as prior art to the present invention.

3. SUMMARY OF THE INVENTION

A method is provided for producing a secondary leachate for use in the production of a product derived or isolated from the secondary leachate comprising:
  a. providing a primary processing bioreactor, a fermentation medium and a microbial culture comprising microorganisms (e.g., bacteria, yeast and/or fungi or combinations thereof, preferably a mixed microbial culture dominated by *Clostridium* spp. and/or *Lactobacillus* spp.);
  b. fermenting the fermentation medium with the microbial culture in the primary processing bioreactor, thereby producing a primary leachate, wherein the primary leachate comprises microorganisms derived from the microbial culture and/or naturally occurring microorganisms acquired during the fermentation step;
  c. isolating or removing the primary leachate from the primary processing bioreactor;
  d. providing a secondary processing bioreactor, *Hermetia illucens* larvae (hereinafter "black soldier fly larvae", "BSFL", or "larvae"), and a cellulose-based substrate;
  e. culturing the BSFL with the primary leachate and the cellulose-based substrate in the secondary processing bioreactor under suboptimal culture conditions for culture of the BSFL, thereby producing a secondary leachate; and
  f. isolating or removing the secondary leachate from the secondary processing bioreactor.

In one embodiment of the method, the product derived or isolated from the secondary leachate is a melanin, a melanin-associated protein, and/or an inorganic fertilizer.

In another embodiment of the method, the product derived from or isolated from the secondary leachate is a reagent or intermediate product for producing melanin, proteins such as melanin-associated proteins, phosphate, ammonia, bicarbonate, inorganic nitrogen (e.g., ammonium, nitrite, nitrate), micronutrients and/or microelements.

In another embodiment of the method, the method additionally comprises the step of:
  g. extracting, isolating or deriving the melanin, melanin-associated protein and/or inorganic fertilizer from the secondary leachate.

In another embodiment of the method, the melanin is selected from the group consisting of pyomelanin, eumelanin and pheomelanin.

In another embodiment of the method, the melanin-associated protein is associated with the melanin.

In another embodiment of the method, the inorganic fertilizer comprises ammonium, phosphate, carbonate, microelements and/or micronutrients.

In another embodiment of the method, the step of extracting, isolating or deriving the melanin, melanin-associated protein or inorganic fertilizer comprises the step of evaporating, titrating for changing the pH, filtering, centrifuging, dialyzing and/or lyophilizing the melanin, melanin-associated protein or inorganic fertilizer.

In another embodiment of the method, the step of culturing the BSFL with the primary leachate, the BSFL density is maintained at $35\pm5$ kg/m$^2$.

In another embodiment of the method, the step of culturing the BSFL with the primary leachate further comprises adding BSFL to the secondary processing bioreactor to maintain the BSFL density at $35\pm5$ kg/m$^2$.

In another embodiment of the method, the step of culturing the BSFL with the primary leachate proceeds for 10-20 days.

In another embodiment of the method, the fermentation medium is organic waste.

In another embodiment of the method, the organic waste is food waste, plant waste, compost, cellulosic residues, cellulose-rich waste, starch-rich waste, or protein-rich waste.

In another embodiment of the method, the step of fermenting the fermentation medium with the microbial culture is conducted under anaerobic or microaerobic conditions.

In another embodiment of the method, the microorganisms in the microbial culture are bacteria, yeast and/or fungi.

In another embodiment of the method, the microorganisms in the microbial culture comprise *Clostridium*, *Lactobacillus* and/or *Actetobacter* bacteria.

In another embodiment of the method, the microbial culture is a pure microbial culture or a mixed microbial culture.

In another embodiment of the method, the mixed microbial culture is derived from inoculums produced by fermenting wheat culture medium with fermentation microorganisms. Standard microbiology methods known in the art can be used to purify many strains of *Clostridium*, *Lactobacillus* and *Acetobacter*. *Clostridium* and *Lactobacillus* will generally be more commonly found or frequent in the primary leachate. *Acetobacter* will generally be more commonly found or frequent in the secondary leachate. Fermenting wheat bran with traces of molasses, until a very high microbial density is reached, is one of the simplest methods, among many known in the art, to produce cultures of *Clostridium* and *Lactobacillus*. *Acetobacter* can be grown using standard methods under aerobic conditions in the presence of alcohols. However, the input materials can be highly variable and each feedstock will favor different strains.

In another embodiment of the method, the steps of (a) providing a primary processing bioreactor, a fermentation medium and a microbial culture, (b) fermenting the fermentation medium with the microbial culture in the primary processing bioreactor, thereby producing a primary leachate and (c) isolating or removing the primary leachate from the fermentation medium, are repeated in sequence (a)-(c) at least 1-5 times.

In another embodiment of the method, the method comprises the step of monitoring the chemical composition of the primary leachate.

In another embodiment of the method, the step of monitoring the chemical composition of the primary leachate is conducted prior to the step of isolating or removing the primary leachate from the primary processing bioreactor.

In another embodiment of the method, the step of isolating or removing the primary leachate from the primary processing bioreactor is conducted at a point at which the fermentation becomes inefficient.

In another embodiment of the method, the step of isolating or removing the primary leachate from the primary processing bioreactor is conducted when the pH of the leachate is 3.4-4.0±0.4.

In another embodiment of the method, the step of culturing the BSFL comprises the step of adding an additive or an augmentation solution to the secondary processing bioreactor.

In another embodiment of the method, the additive or augmentation solution comprises carbohydrate, cellulose and/or starch.

In another embodiment of the method, the carbohydrate is a sugar.

In another embodiment of the method, the additive or augmentation solution comprises molasses.

In another embodiment of the method, the suboptimal culture condition is suboptimal temperature, high density, chemical stress, acidification, presence of toxic secondary metabolites, and/or nutrient starvation.

In another embodiment of the method, the step of culturing the BSFL is carried out under a nitrogen-poor condition and/or a phosphorus relative C condition.

In another embodiment of the method, the nitrogen-poor condition or the phosphorus relative C condition is relative to a classical Redfield ratio, wherein the ratio is 106C:16N:1P.

In another embodiment of the method, the bacteria, yeast and/or fungi in the secondary processing bioreactor are derived from the primary leachate or are naturally occurring.

In another embodiment of the method, after the step of isolating or removing the secondary leachate from the secondary processing bioreactor, new primary leachate and/or additional BSFL are added to the secondary processing bioreactor.

In a specific embodiment, the method can be used to produce a melanin, a melanin-associated protein or an inorganic fertilizer and comprises the steps of:
  a. providing a primary processing bioreactor, a fermentation medium and a microbial culture comprising microorganisms;
  b. fermenting the fermentation medium with the microbial culture in the primary processing bioreactor, thereby producing a primary leachate, wherein the primary leachate comprises microorganisms derived from the microbial culture and/or naturally occurring microorganisms acquired during the fermentation step;
  c. isolating or removing the primary leachate from the primary processing bioreactor;
  d. providing a secondary processing bioreactor, *Hermetia illucens* larvae (BSFL), and a cellulose-based substrate;
  e. culturing the BSFL with the primary leachate and the cellulose-based substrate in the secondary processing bioreactor under suboptimal culture conditions for culture of the BSFL, thereby producing a secondary leachate;
  f. isolating or removing the secondary leachate from the secondary processing bioreactor; and
  g. extracting, isolating or deriving the melanin, melanin-associated protein or inorganic fertilizer from the secondary leachate.

A primary processing bioreactor for fermenting food and vegetal wastes and for producing primary leachate is also provided.

A secondary processing bioreactor for converting primary leachate to secondary leachate is also provided.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated, enlarged, exploded, or incomplete to facilitate an understanding of the invention.

FIG. 1. Diagram of redox changes in one unit of pyomelanin, showing that each unit can exist in three oxidation-reduction states: quinone, semiquinone and hydroquinone.

Figure 2:
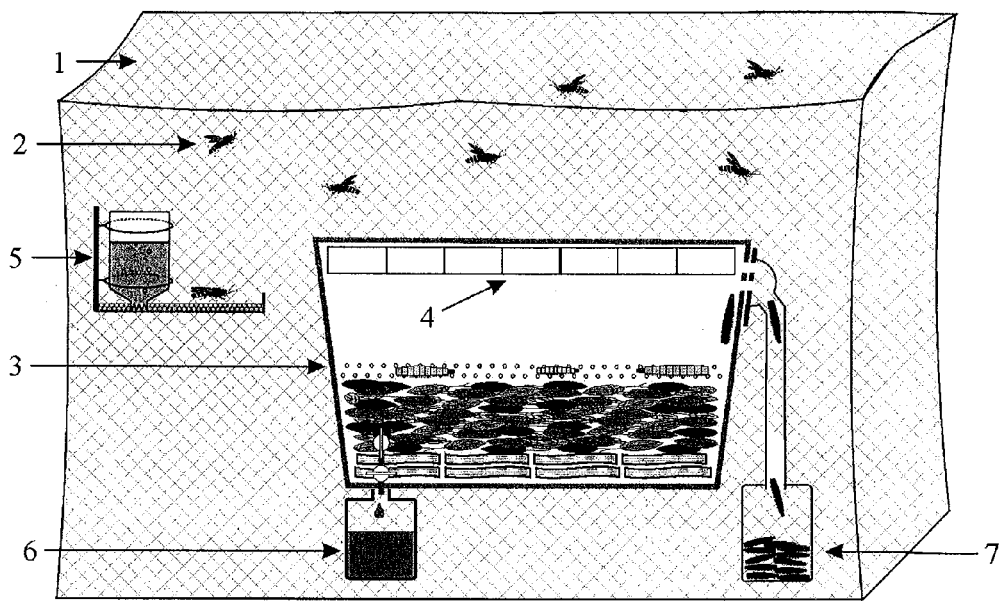

FIG. 2. Cross-sectional diagram of an embodiment of a black soldier fly (BSF) nursery used to produce and harvest eggs of BSF. Nurseries can be scaled up or down to suit a wide range of production schemes and can have controlled environmental conditions. The nursery is constructed with screen to hold the flies and BSF larvae (BSFL) inside (1), and contains adult BSF (2), larvae feeding containers (3), egg laying substrates (4), water source (5), secondary leachate collectors (6) and larvae collectors (7). Not shown in this diagram are additional elements that can be employed such as temperatures controllers, moisture controllers, air purifiers and traps for gnats and houseflies.

Figure 3:
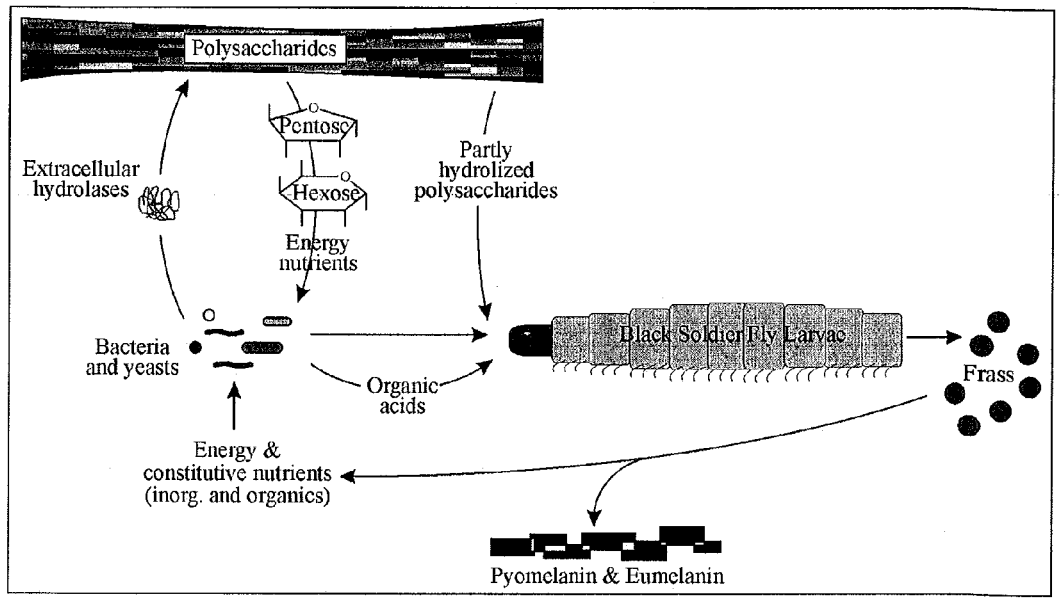

FIG. 3. Diagram illustrating principle of one embodiment of the method disclosed herein, which is used to convert media rich in sugars and polysaccharides (comprised in primary leachate) in solutions with high concentration of pyomelanin (comprised in secondary leachate).

Figure 4:
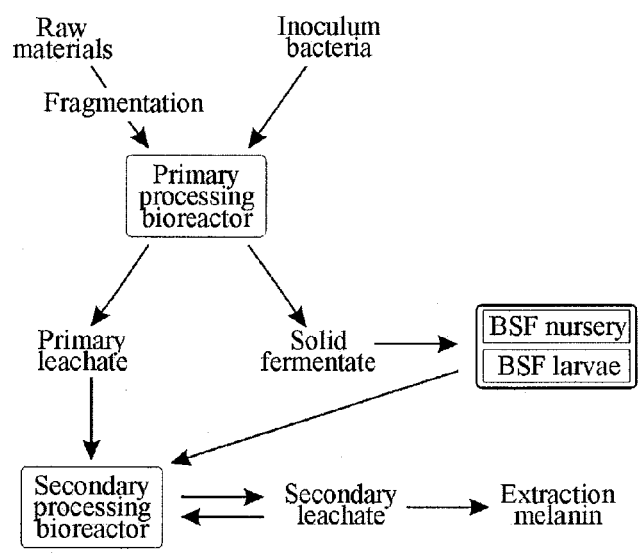

FIG. 4. Flow diagram of one embodiment of the method disclosed herein. In this embodiment, the method is used to convert raw materials (e.g., food waste, residues of food industry; gardening and agriculture vegetal waste) into pyomelanin.

Figure 5:
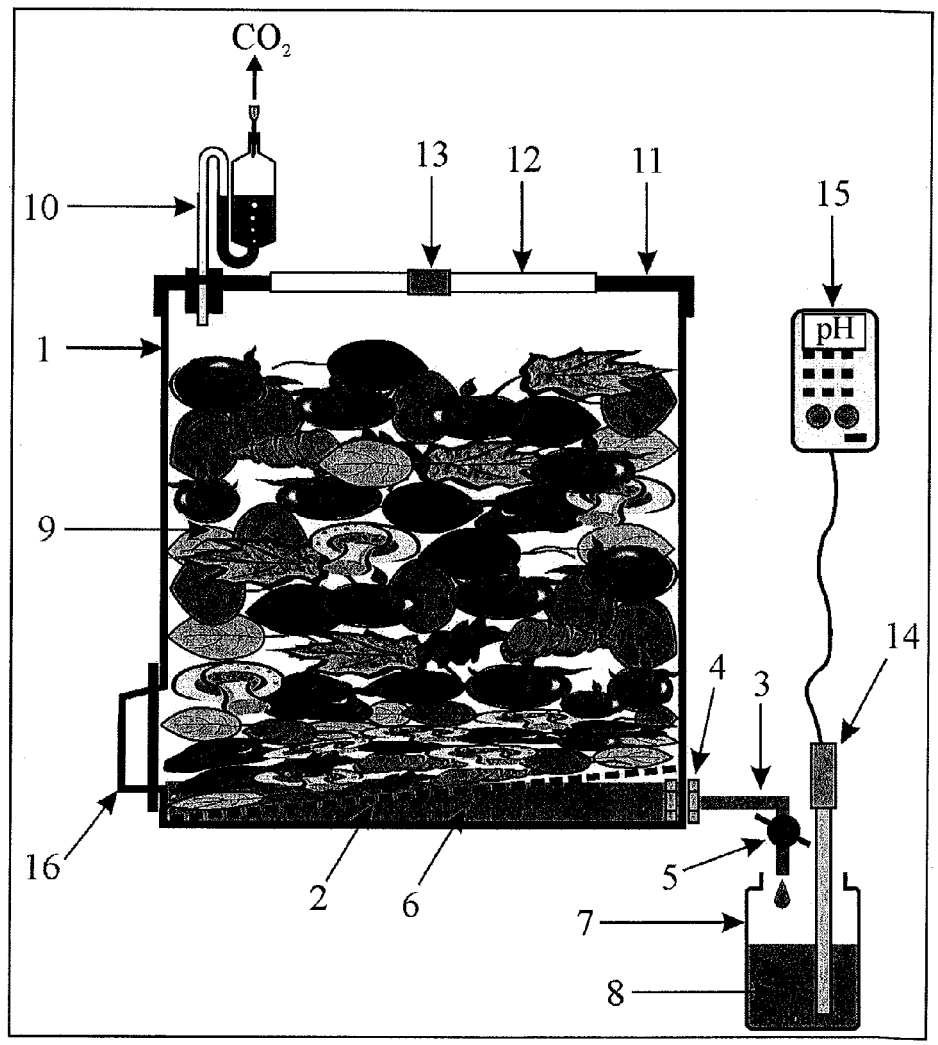

FIG. 5. Cross-sectional diagram of an embodiment of a primary processing bioreactor for fermenting food and vegetal wastes and for producing primary leachate. (1) Side wall of the primary processing bioreactor. (2) Bottom sieve. (3) Primary leachate drainage tube. (4) Drainage system fitting. (5) Drainage system spigot. (6) Primary leachate accumulated in the primary processing bioreactor. (7) Primary leachate collecting container. (8) Primary leachate in collecting container. (9) Vegetal materials and food waste processed in the primary processing bioreactor. (10) Gas outflow system used to monitor the production of gases produced during fermentation (primarily carbon dioxide). (11) Main primary processing bioreactor lid used for cleanup. (12) Secondary primary processing lid, which can be used to add new fermentable materials and lime during fermentation. (13) Port, which can be used for injecting water, buffers, augmentation ingredients (e.g., molasses) and microbial inocula as needed during fermentation and for returning to the primary processing bioreactor any primary leachate that is insufficiently acidic or is poor in nutrients. (14) Electrode for monitoring the pH of the primary leachate. (15) pH meter. (16) Side gate for the collection of solid fermented materials.

FIG. 6. Cross-sectional diagram of an embodiment of a secondary processing bioreactor comprising wood shavings, organotrophic bacteria, yeasts and Black Soldier Fly larvae (also referred to herein as "BSFL," "BSF larvae" or "larvae"). The secondary processing bioreactor can be used to convert primary leachate to secondary leachate rich in melanin, melanin-associated proteins and inorganic fertilizer. (1) Rear or back side of the secondary processing bioreactor. (2) Exit ramp for mature (wandering) BSFL. This embodiment has an approximately 30-60° slope angle. (3) Larvae exit path. (4) Lid for adding more materials as needed (e.g., additional primary leachate, young larvae and/or an augmentation ingredient or additive such as molasses). (5) Secondary leachate drainage tube. (6) Drainage system fitting. (7) Drainage system spigot. (8) Secondary leachate in the secondary processing bioreactor. (9) Collection container with secondary leachate enriched in melanin. (10) Light, solid, slowly decaying, non-toxic substrate material such as wood shavings. (11) BSFL crawling on top. (12) BSFL processing the primary leachate into secondary leachate. (13) BSFL crawling out of the processor (in the wandering stage) when they have reached maturity. (14) Air pump for aerating the bottom portion of the primary leachate being converted into secondary leachate and to circulate the leachate inside the secondary processing bioreactor. (15) Air pump for providing air to the BSFL. (16) Electrode for monitoring the pH of the leachate (i.e., primary leachate being converted into secondary leachate). (17) pH meter.

FIGS. 7A-C. The effect of the fermentate composition and leachate treatment on the pH of the primary leachate (modified after Alattar et al., 2012). The graphs show the evolution of pH in primary processing bioreactors with three treatments: A) Primary leachate continuously eliminated; B) Primary leachate returned un-aerated to the fermentors; and C) Primary leachate aerated for three days then returned to the primary processing bioreactor. A1, A2 and A3 are incubations of 100% lignocellulose materials and 0% produce. B, B2 and B3 are incubations of 90% lignocellulose materials and 10% produce. C1, C2 and C3 are incubations of 50% lignocellulose materials and 50% produce.

FIGS. 8a-b. (a) The effect of BSFL on the evolution of pH and Chemical Oxygen Demand (COD) while feeding on compost primary leachate: $\Delta$=pH without BSFL; $\blacktriangle$=pH with BSFL; $\square$=COD without BSFL; and $\blacksquare$=COD with BSFL. Errors bars are ±1SD of duplicates using 20 BSFL in 10 ml primary leachate. (b) The turnover of the dominant VOAs and alcohols from primary leachate±BSFL, using ten larvae per 2 ml primary leachate: Et=ethanol; nP=n-propanol; Ac=acetic acid; Pr=propanoic acid; Bu=butyric acid; and Is=isovaleric acid (Popa and Green, 2012).

5. DETAILED DESCRIPTION OF THE INVENTION

For clarity of disclosure, and not by way of limitation, the detailed description of the invention is divided into the subsections set forth below.

5.1. Black Soldier Flies (BSF)

Black soldier flies (BSF), *Hermetia illucens*, are insects in the order Diptera. BSF are ubiquitous throughout much of the world extending between roughly the equator and 45th degree latitude (Newton et al., J. Anim Sci., 44:395-400, 1977; Bondari and Sheppard, Aquaculture and Fisheries Management, 18:209-220, 1987; Sheppard et al., Bioresource Technology, 50:275-279, 1994; Tomberlin et al., Ann. Entomol. Soc. Am., 95:379-386, 2002; St-Hilaire et al., J. World Aquaculture Society, 38:59-67, 2007; St-Hilaire et al., J. World Aquaculture Society, 38:309-313, 2007). They are holometabolous insects that undergo a life cycle of complete metamorphosis. The life cycle progresses from the egg to hatching of the larva, typically 5-6 larval instars or stages, pre-pupa, pupation into the pupal stage, then ecdysis (emergence) into the adult fly. During the pre-pupa stage, between the larva and pupal stages, the larva enters the wandering stage, moves away from or out of the nutrient source to find a pupation site on a dry surface. The skilled artisan is familiar with larvae generally, and with methods of breeding and propagating larvae. For example, methods of breeding and propagating dipterans including *Hermetia illucens* larvae can be found, e.g., in Fatchurochim et al., J. Entomol. Sci., 24:224-231, 1989).

Methods of breeding and propagating black soldier fly larvae (BSFL), including methods of breeding BSFL in captivity, as well as methods for using BSFL to process solid wastes and organic leachates, are familiar to the skilled artisan (see for example, Tomberlin et al., Environ Entomol., 38 (3):930-4, 2009; Sheppard et al., J. Med. Entomol., 39 (4): 695-8, 2002; Tomberlin, J. Econ. Entomol., 95:598-602, 2002; U.S. Pat. No. 6,780,637; US 2012/0187041; Popa et al., J. Econ. Entomol., 105(2): 374-378, 2012).

Additionally, BSFL can be purchased commercially, for example BioGrubs™ BSFL (Prota Culture, LLC, Dallas, Tex.) and Phoenix Worms™ BSFL (Insect Science Resource, LLC, Tifton, Ga.). Alternatively, BSFL, and eggs laid by adults, can be harvested in the wild by gathering eggs and larvae present in animal manure, particularly chicken and pig manure, on farms and at commercial animal facilities open to the elements, especially in warmer climates where the insects are known to lay eggs throughout the year in the wild.

BSF eggs take approximately 4 days to hatch and are typically deposited in crevices or on surfaces above or adjacent to the food source. BSFL approaching the pupae stage reach a size in excess of 2 cm in length and 0.4 cm in diameter relative to immature larvae which start out on hatching from eggs at less than 0.2 cm in length and less than 0.1 cm in diameter. Although they can be stored at room temperature for several weeks, their longest shelf life is achieved at 50-60° F. (10-16° C.).

BSFL feed on a variety of vegetal and manure wastes of varying extreme pH ranges and $O_2$ tensions, self-harvest on entering the pupae stage from the organic matter they are feeding on, and are ubiquitous throughout much of the world extending between roughly the equator and 45th degree latitude (Newton et al., J. Anim Sci., 44:395-400, 1977; Bondari and Sheppard, Aquaculture and Fisheries Management, 18:209-220, 1987; Sheppard et al., Bioresource Technology, 50:275-279, 1994; Tomberlin et al., Ann. Entomol. Soc. Am., 95:379-386, 2002; St-Hilaire et al., J. World Aquaculture Society, 38:59-67, 2007; St-Hilaire et al., J. World Aquaculture Society, 38:309-313, 2007). BSF larva consume organic matter, including kitchen waste, spoiled feed, and manure, and assimilates organic compounds in the organic matter into larva biomass. BSFL, like most dipteran insects, wander out of, or "self-harvest" from, the organic matter they are feeding on upon entering the pupal stage. Adult BSF do not need to eat; they survive on the fat stored from the larva stage.

Prior to their introduction into the step of the method of culturing the BSFL with primary leachate, as described hereinbelow, BSFL can be hatched from egg clutches laid by mating adult flies in an insect nursery (FIG. 2) set up for rearing flies on decomposing vegetal and food scrap residues (banana peelings, leftover fragments of lettuce, stale bread, rotting tomatoes, apples, and other discarded produce, yard debris including mowed grass clippings, etc.) under conditions known in the art (Tomberlin et al., Environ Entomol., 38 (3):930-4, 2009). The eggs can be hatched in wheat bran moistened with tap water. At approximately 1 week of age, larvae can be freed of wheat bran by washing them in stainless steel mesh colander (mesh size 1 mm) with several liters of tap water.

FIG. 2 is a diagram of an embodiment of a black soldier fly (BSF) nursery used to produce and harvest eggs of BSF. Nurseries can be scaled up or down to suit a wide range of production schemes.

5.2. Method for Producing Melanin, Melanin-Associated Protein and/or Inorganic Fertilizers from Fermentation Leachates A method is provided for producing melanin, melanin-associated protein and/or inorganic fertilizers from fermentation leachates or from low-cost nutrient-rich solutions. The method for producing the melanin or inorganic fertilizer comprises repetitive trophic cycling, under the controlled conditions of bioreactors, of nutrients between organisms with complementary physiology: natural microorganisms such as bacteria, yeast and fungi and larvae of *Hermetia illucens*, the Black Soldier Fly (BSF). According to the method, polysaccharides are partly converted into natural melanins or inorganic fertilizer, which are difficult to biodegrade and hence accumulate in the bioreactors. The method can employ, as a source of nutrients, leachates produced from food waste and sugars-rich liquid waste of the food industry. These leachates can be used raw or they can be augmented with low-cost sugar-rich solutions such as molasses, hydrolyzed cellulose or starch. The method is inexpensive and does not require the use of expensive chemically-defined culture media.

Diagrams of one embodiment of the method are shown in FIGS. 3 and 4. FIG. 3 shows an overview of the method used to convert media rich in sugars and polysaccharides (comprised in primary leachate) in solutions with high concentration of melanin, including but not limited to pyomelanin (comprised in secondary leachate). FIG. 4 is a flow diagram showing an embodiment of the method that can be used to convert raw materials (e.g., food waste, residues of food industry; gardening and agriculture vegetal waste) into melanin, including but not limited to pyomelanin. Bacteria from the mixed culture produce extracellular cellulases which hydrolyze cellulose and hemicellulose to sugars (hexoses and pentoses). Along with other sugars present in the primary leachate, these added sugars are used by microorganisms (e.g., bacteria and fungi) as a source of energy and carbon. During growth, microorganisms uptake nutrients and produce biomass and secondary metabolites (mostly organic acids, alcohols and amines). These microorganisms also produce melanin. BSFL grind partly digested polysaccharides in order to uptake digestible organics and microbial biomass and also consume microbial biomass and metabolites directly from liquid. BSFL do not digest cellulosic polysaccharides, but they grind larger particles into finer particles making them more prone to enzymatic hydrolysis. BSFL eliminate unused food in the form of a finely ground suspensions called frass (i.e., 20-200 μm diameter colloids), thus returning nutrients (C, N, P, S, etc.) and bioavailable energy to the medium. This recycling of nutrients and the removal of toxic metabolites make microorganisms divide indefinitely as long as the primary carbon and energy sources are available. As they grow, microorganisms continuously produce polyphenols (such as melanin), but neither BSFL nor microorganisms digest polyphenols efficiently. In this system melanins are not recycled, but they accumulate.

In an exemplary, non-limiting embodiment of the method, a method is provided for producing a secondary leachate for use in the production of a product derived or isolated from the secondary leachate comprising:
  a. providing a primary processing bioreactor, a fermentation medium and a microbial culture comprising microorganisms (e.g., bacteria, yeast and/or fungi or combinations thereof, preferably a mixed microbial culture dominated by *Clostridium* spp. (also referred to herein as "*Clostridium*") and/or *Lactobacillus* spp. (also referred to herein as "*Lactobacillus*"),
  b. fermenting the fermentation medium with the microbial culture in the primary processing bioreactor, thereby producing a primary leachate, wherein the primary leachate comprises naturally occurring microorganisms acquired during the fermentation step;
  c. isolating or removing the primary leachate from the primary processing bioreactor;
  d. providing a secondary processing bioreactor, *Hermetia illucens* larvae (hereinafter "black soldier fly larvae" or "BSFL"), and a cellulose-based substrate;
  e. culturing the BSFL with the primary leachate and the cellulose-based substrate in the secondary processing bioreactor under suboptimal culture conditions for culture of the BSFL, thereby producing a secondary leachate; and
  f. isolating or removing the secondary leachate from the secondary processing bioreactor.

In one embodiment of the method, the product derived or isolated from the secondary leachate is melanin, a melanin-associated protein, or an inorganic fertilizer.

In another embodiment of the method, the product derived or isolated from the secondary is a reagent or intermediate product for producing melanin, proteins, phosphate, ammonia, bicarbonate, inorganic nitrogen (e.g., ammonium, nitrite, nitrate), micronutrients and/or microelements.

In another embodiment of the method, the method additionally comprises the step of:
  g. extracting, isolating or deriving the melanin, melanin-associated protein and/or inorganic fertilizer from the secondary leachate.

In another embodiment, a method is provided for producing a melanin, a melanin-associated protein and/or an inorganic fertilizer, comprising the steps of:
  a. providing a primary processing bioreactor, a fermentation medium and a microbial culture comprising microorganisms (e.g., bacteria, yeast and/or fungi or combinations thereof, preferably a mixed microbial culture dominated by *Clostridium* and/or *Lactobacillus*);
  b. fermenting the fermentation medium with the microbial culture in the primary processing bioreactor, thereby producing a primary leachate, wherein the primary leachate comprises microorganisms derived from the microbial culture and/or naturally occurring microorganisms acquired during the fermentation step;
  c. isolating or removing the primary leachate from the primary processing bioreactor;
  d. providing a secondary processing bioreactor, *Hermetia illucens* larvae (hereinafter "black soldier fly larvae", "BSFL", or "larvae"), and a cellulose-based substrate;
  e. culturing the BSFL with the primary leachate and the cellulose-based substrate in the secondary processing bioreactor under suboptimal culture conditions for culture of the BSFL, thereby producing a secondary leachate;
  f. isolating or removing the secondary leachate from the secondary processing bioreactor; and g. extracting, isolating or deriving the melanin, melanin-associated protein or inorganic fertilizer from the secondary leachate.

5.2.1. Providing a Primary Processing Bioreactor, a Fermentation Medium and a Microbial Culture Comprising Microorganisms In the first step of the method, a primary processing bioreactor, a fermentation medium and a microbial culture comprising microorganisms (e.g., bacteria, yeast and/or fungi or combinations thereof, preferably a mixed microbial culture dominated by *Clostridium* spp. and/or *Lactobacillus* spp.), are provided.

The primary processing bioreactor is an incubator for converting food waste and vegetal residues into primary leachate via fermentation. An embodiment of a primary processing bioreactor is shown in FIG. 5. Microorganisms (MOs) used in the primary processing bioreactor can be naturally occurring bacteria, preferably from the genera *Clostridium* and *Lactobacillus*. The role of *Clostridium* is to produce exoenzymes digesting polysaccharides such as cellulose and starch. The role of *Lactobacillus* is to ferment sugars and to lower the pH of the primary leachate making it shelf stable in anaerobiosis. This process is akin to pickling or silage.

In one embodiment, the fermentation medium is organic waste, such as food waste, plant waste, compost, cellulosic residues, cellulose-rich waste, starch-rich waste, or protein-rich waste. Carbohydrates (particularly polysaccharides) are most important in this process because they can be used by microorganisms as a source of energy, yet have little value as feedstock for the BSFL. Vegetal wastes that are rich in sugars, starch and cellulosic polymers are particularly preferred. Vegetal wastes that are very rich in cellulose but poor in sugars and starch (such as hay, straw or corn stover), can be used, but are of lesser value because they do not decompose fast enough in the primary processing bioreactor (FIG. 3, also referred to herein as "primary bioreactor"). Woody biomass (which is very rich in lignin) cannot be processed by this method, though it can be used as filler or for increasing permeability in primary bioreactors (FIG. 5). Wood shavings are also used in the secondary bioreactors (FIGS. 3 and 6, also referred to herein as "secondary processing bioreactors") as a crawling substrate for the larvae.

Animal waste, dairy products and animal and vegetal fats are preferably present in low proportion (<5%) in the primary bioreactors, should be fed directly to the larvae from the nursery (FIGS. 2 and 5) and should not be used in the secondary bioreactors. BSFL can eat animal waste, but prefer a mixed diet, which includes vegetal waste as well Animal carcasses, bones, skins, entrails, oils, grease and dairy products aggravate management, odor and pest problems, and greatly increase health risks due to food-borne pathogens such as *Salmonella, Listeria, E. coli* and *Campylobacter* (to name only a few). Sewage liquid and sludge are not recommended as feedstock because they are also a health hazard. They are also inefficient in the production of melanin because they are eaten by both microorganisms and BSFL, and because they do not stunt the growth of the larvae. Stunting the growth of the larvae in the secondary bioreactors is very important, because it helps limit the removal of nutrients and energy in the form of mature larvae biomass and lowers the amount of newborn larvae that have to be constantly produced. Manure, used in excess, increases the risk of spreading coliforms and other pathogens (especially if the larvae produced in this process are to be later used as feedstock for animals). Excessive use of manure will also aggravate odor problems (due primarily to ammonia and organic amines).

The types of raw materials preferred for this process include, but are not limited to, non-animal derived food waste (from groceries, bakeries, restaurants, domestic sources and food industry) and vegetal waste (green biomass from vegetable farms and greenhouses, aquaponics and hydroponic stations, leaves and grass clippings). Products such as manure, hay, straw and soiled animal bedding can also be used, but only to a lesser extent and should be mixed with the above recommended raw materials.

The microbial culture comprises bacteria, yeast and/or fungi. In a preferred embodiment, the microorganisms in the microbial culture are species of *Clostridium* and *Lactobacillus* bacteria. In another embodiment, the microbial culture is a pure microbial culture or a mixed microbial culture. Numerous methods are known in the art for growing *Clostridium* and *Acetobacter*. Fermenting wheat bran with traces of molasses, until very high microbial density is reached, is one of the simplest. Thus, in a specific embodiment, the mixed microbial culture is derived from inoculums produced by fermenting wheat culture medium with fermentation microorganisms.

5.2.2. Fermenting the Fermentation Medium with the Microbial Culture in the Primary Processing Bioreactor In the next step of the method, the fermentation medium is fermented with the microbial culture in the primary processing bioreactor thereby producing a primary leachate, wherein the primary leachate comprises microorganisms derived from the microbial culture and/or naturally occurring microorganisms acquired during the fermentation step. The primary leachate is thus a liquid byproduct of anaerobic fermentation of the organic waste.

The step of fermenting the fermentation medium with the microbial culture can be conducted under anaerobic or microaerobic conditions.

The method can additionally comprise the step of monitoring the chemical composition of the primary leachate. Preferably, the step of monitoring the chemical composition of the primary leachate is conducted prior to the step of isolating or removing the primary leachate from the primary processing bioreactor.

5.2.3. Isolating or Removing the Primary Leachate from the Primary Processing Bioreactor In the next step of the method, the primary leachate is isolated or removed from the primary processing bioreactor (FIG. 5). This can be accomplished by many methods known in the art, such as by draining, pumping, etc. In one embodiment, the step of isolating or removing the primary leachate from the primary processing bioreactor is conducted at a point at which the fermentation becomes inefficient, which can be determined using methods known in the art. For example, the pH can be measured with a pH meter. Acidification, i.e., accumulation of organic acids (mainly acetic acid), changes the pH and can stop the fermentation. The concentration of organic acids and alcohols can also be measured to determine inefficient fermentation, using methods known in the art. Sugars (mono and disaccharides) can be measured by standard methods of liquid chromatography, gas chromatography, colorimetric methods and spectroscopy.

In another embodiment, the step of isolating or removing the primary leachate from the primary processing bioreactor is conducted when the pH of the primary leachate is 3.4-4.0±0.4.

In a preferred embodiment, the steps of (a) providing a primary processing bioreactor, a fermentation medium and a microbial culture, (b) fermenting the fermentation medium with the microbial culture in the primary processing bioreactor, thereby producing a primary leachate and (c) isolating or removing the primary leachate from the fermentation medium, are repeated in sequence (a)-(c) at least 1-5 times. After this many repetitions, the food source can become exhausted and can be removed from the primary incubator and replaced.

5.2.4. Providing a Secondary Processing Bioreactor, *Hermetia Illucens* Larvae (BSFL) and a Carbohydrate-Based Substrate In the next step of the method, a secondary processing bioreactor, *Hermetia illucens* larvae (BSFL) and a carbohydrate-based substrate are provided. The secondary processing bioreactor (FIG. 6) can contain wood shavings, organotrophic bacteria, yeasts and BSFL. The secondary processing bioreactor (also referred to herein as "secondary bioreactor") can be used to convert primary leachate into melanin-rich secondary leachate. (1) Rear or back side of the secondary processing bioreactor. (2) Exit ramp for mature (wandering) BSFL. This embodiment has an approximately 30-60° slope angle. (3) Larvae exit path. (4) Lid for adding more materials as needed (e.g., additional primary leachate, young larvae and/or molasses). (5) Secondary leachate drainage tube. (6) Drainage system fitting. (7) Drainage system spigot. (8) Secondary leachate in the secondary bioreactor. (9) Collection container with secondary leachate enriched in melanin. (10) Light, solid, slowly decaying, non-toxic substrate material such as wood shavings. (11) BSFL crawling on top. (12) BSFL processing the primary leachate into secondary leachate. (13) BSFL crawling out of the processor (in the wandering stage) when they have reached maturity. (14) Air pump for aerating the bottom portion of the leachate and to circulate the primary leachate inside the secondary processing bioreactor. In the beginning of secondary processing the leachate will be primary leachate, which in time will be converted into secondary leachate. (15) Air pump for providing air to the BSFL. (16) Electrode for monitoring the pH of the leachate (i.e., primary leachate being converted into secondary leachate). (17) pH meter.

The carbohydrate-based substrate is preferably rich in sugars, and can be, for example, molasses, starch, cellulose (e.g., hydrolyzed cellulose), wood-chips or wood shavings and/or combinations thereof. Wood chips or shavings are particularly preferred as a substrate.

5.2.5. Culturing the BSFL with the Primary Leachate and the Carbohydrate-Based Substrate in the Secondary Processing Bioreactor Under Suboptimal Culture Conditions In the next step of this embodiment of the method, the BSFL are cultured with the primary leachate and the carbohydrate-based substrate in the secondary processing bioreactor under suboptimal culture conditions for culture of the BSFL, thereby producing a secondary leachate.

In another embodiment, in the step of culturing the BSFL with the primary leachate and the carbohydrate-based substrate, the BSFL density is maintained at $35\pm5$ kg/m$^2$.

In another embodiment, the step of culturing the BSFL with primary leachate and the carbohydrate-based substrate further comprises adding BSFL to the secondary processing bioreactor to maintain the BSFL density at $35\pm5$ kg/m$^2$.

As mentioned above, wood chips or shavings are particularly preferred as the carbohydrate-based substrate, as very high densities of BSFL can be maintained in cultures containing wood chips/shavings. In a preferred embodiment, a density of at least 500,000 larvae/m$^2$ is maintained. In other embodiments, larval density is 2-4 kg/ft$^2$.

In another embodiment, the step of culturing the BSFL with the primary leachate proceeds for 10-20 days.

In another embodiment, the step of culturing the BSFL with the primary leachate comprises the step of adding an additive to the secondary processing bioreactor. The additive, which can be a solid, liquid, or a gas, can be used to augment the components being cultured in the secondary processing bioreactor. When the additive is a liquid or is added as a solution to the culture, it is also referred to herein as an "augmentation solution." The additive can comprise carbohydrate (e.g., sugar), cellulose and/or starch. In another embodiment, the carbohydrate is a sugar, e.g., a monosaccharide or a disaccharide sugar. In specific embodiments, the sugar is glucose, fructose, galactose, sucrose, maltose and/or lactose. In another specific embodiment, the additive is molasses. In other embodiment, the additive can be any organic molecule, polymer or small metabolite that is known in the art to promote or assist the growth of bacteria, yeast and/or fungi can be amino acids, pentoses, proteins, nucleic acids, carboxylic acids, etc.

An additive or augmentation solution could be added, for example, upon a decrease in biological oxygen demand, when no change in pH of the leachate being processed by the BSFL is observed or when very little change in melanin yield or concentration is seen over time compared with earlier rounds of culturing.

Air can also be an additive that is pumped into the secondary processing bioreactor to provide air to the BSFL. Due to high density, the BSFL may run out of oxygen. White BSFL crawling out of the secondary bioreactor can be evidence of lack of food provided by the primary leachate, or more likely, excess carbon dioxide and lack of oxygen.

The bacteria, yeast or fungi in the secondary processing bioreactor can be comprised in the primary leachate or can be naturally occurring and introduced naturally from the environment into the culture in the secondary processing bioreactor.

The step of culturing the BSFL with the primary leachate is preferably carried out under suboptimal culture conditions for the growth of the BSFL. Suboptimal culture conditions for BSFL are known in the art and can be, for example, suboptimal temperature, high density, chemical stress, acidification, presence of toxic secondary metabolites, and/or nutrient starvation. All of these conditions delay metamorphosis and force the BSFL to remain as larvae for a prolonged period of time. Whereas BSFL would normally pupate after approximately 14-21 days as larvae, under suboptimal culture conditions they can remain as larvae as long as 2-6 months.

In one embodiment, the step of culturing the BSFL is carried out under nitrogen-poor or phosphorus relative C conditions as compared to the classical Redfield ratio of approximately C:N:P=106:16:1. Such nitrogen-poor or phosphorus relative C conditions as compared to the classical Redfield ratio can be determined by one of skill in the art.

5.2.6. Isolating or Removing the Secondary Leachate from the Secondary Processing Bioreactor.

In the next step of this embodiment of the method, the secondary leachate is isolated or removed from the secondary processing bioreactor. In one embodiment, the secondary leachate is isolated or removed by draining using methods known in the art. For example, a preferred method is to drain the liquid through a spigot placed near the bottom of the secondary processing bioreactor. In certain embodiments, e.g., embodiments using a large secondary processing bioreactor, a pump can be added to facilitate drainage.

In another embodiment, after the step of isolating or removing the secondary leachate from the secondary processing bioreactor, new primary leachate and/or additional BSFL are added to the secondary processing bioreactor.

5.2.7. Extracting, Isolating or Deriving the Melanin, Melanin-Associated Protein or Inorganic Fertilizer from the Secondary Leachate In certain embodiments of the method, melanin, melanin-associated protein or inorganic fertilizer is extracted, isolated or derived from the secondary leachate. In another embodiment, the step of extracting, isolating or deriving the melanin, melanin-associated protein or inorganic fertilizer comprises the step of evaporating, titrating for changing the pH, filtering, centrifuging, dialyzing and/or lyophilizing the melanin, melanin-associated protein or inorganic fertilizer. Such methods are commonly known in the art.

5.2.8. Melanins and Melanin-Associated Proteins

The methods disclosed herein can be used to produce melanins. Melanins are a class of natural polyphenols composed mainly of carbon, oxygen, hydrogen, nitrogen and sulfur and made of monomers derived from aromatic amino acids (tyrosine and phenylalanine). At the macromolecular level (primary, secondary and tertiary structure level) melanins are a family of molecules and do not have a single chemical structure and molecular size. The method disclosed herein produces a mixture of melanins comprising pyomelanin, eumelanin and pheomelanin. Melanins comprise melanin monomers, which are chemical derivatives of tyrosine. Pyomelanin comprises homogentisate monomers. Eumelanin comprises DOPA monomers.

Thus, in one embodiment of the method, the melanin is selected from the group consisting of pyomelanin, eumelanin and pheomelanin.

Melanins are known in the art to be associated with melanin-associated proteins. Melanin-associated proteins form complexes with melanins and are commonly present in melanin extracts. In one embodiment, the melanin produced by the method is isolated with or without its melanin-associated protein(s) associated with the melanin. The melanin-associated proteins can be isolated in association with the melanin or separately from the melanin using methods known in the art.

Since melanin-associated proteins have a selective affinity for melanin, they can be used as "molecular handles", using methods known in the art, to tether or immobilize melanin to a substrate, such as nanoparticles (e.g., magnetic or fluorescently-labeled nanoparticles, microbeads, microvesicles, electrode tips, membranes or any other substrate known in the art to be suitable for binding, or being associated with, a tethering protein.

Methods for isolating melanin are well known in the art. Melanins can be isolated with or without their associated proteins. The following references are a sample of methods known in the art for isolating melanin and melanin-associated proteins from organisms. The skilled practitioner can easily adapt these methods for isolating melanin from secondary leachate:

Araujo et al., 2012, Marine sponge melanin: a new source of an old biopolymer, Structural Chemistry, 23:115-122.

Chen et al., 2008, 2008, Isolation and characterization of natural melanin derived from silky fowl (*Gallus gallus domesticus Brisson*), Food Chemistry, 111:745-749.

Crippa et al., 1989, Chemistry of melanins, The Alkaloids 36:253-322, Academic Press, N.Y., N.Y.

Dong and Yao., 2012, Isolation, characterization of melanin derived from *Ophiocordyceps sinensis*, an entomogenous fungus endemic to the Tibetan Plateau, Journal of Bioscience and Bioengineering, 113:474-479.

Harki et al., 1997, Purification, characterisation and analysis of melanin extracted from *Tuber melanosporum* Vitt., Food Chemistry, 58:69-73.

Liu et al., 2003, Comparison of the structural and physical properties of human hair eumelanin following enzymatic or acid/base extraction, Pigment Cell Research, 16:355-365.

Loganathan and Kalyanasundaram, 1999, The melanin of the myxomycete *Stemonitis herbatica*, Acta Protozoologica, 38:97-103.

Medes et al., 1928, Proceedings of the Society for Experimental Biology and Medicine, 25:635-637.

Prota, 1988, Progress in the chemistry of melanins and related metabolites, Medical Research Reviews, 8:525-556.

Ravishankar et al., 1995, Isolation and characterization of melanin from a marine fungus, Botanica Marina, 38:413-416.

Rosas et al., 2000, Isolation and serological analyses of fungal melanins, Journal of Immunological Methods, 244:69-80.

Zeise et al., 1992, Melanin standard method—particle description, Pigment Cell Research, 5:132-142.

Zou et al., 2010, Optimization of ultrasound-assisted extraction of melanin from *Auricularia auricula* fruit bodies, Innovative Food Science & Emerging Technologies, 11:611-615.

Young, 1921, The extraction of melanin from skin with dilute alkali, Biochemical Journal., 15:118-122.

Wakamatsu and Ito, 2002, Advanced chemical methods in melanin determination, Pigment Cell Research, 15:174-183.

Wang et al., 2006, Isolation and characterization of melanin from *Osmanthus fragrans* seeds, LWT-Food Science and Technology, 39:496-502.

Wheeler et al., 1978, Ultrastructural and chemical distinction of melanins formed by *Verticillium dahlia*, from (+)-scytalone, 1,8-dihydroxynaphthalene, catechol, and $_L$-3,4-dihydroxyphenylalanine, Can. J. Microbiol., 24:289-297.

5.2.9. Methods for Isolating Inorganic Fertilizers

The methods disclosed herein can also be used to produce inorganic fertilizers. Inorganic fertilizers are inorganic molecules rich in carbon, nitrogen, phosphorus, potassium and microelements and/or micronutrients. The inorganic fertilizer produced by the method disclosed herein can comprise ammonium, phosphate, carbonate and/or micronutrients. In certain embodiments, the inorganic fertilizer obtained using the methods disclosed herein can include, but are not limited to:

Phosphate rich minerals, for example, a mixture dominated by struvite ($NH_4MgPO_4.6H_2O$), but can comprise, in other embodiments, other precipitates with phosphorus such as calcium phosphates ($Ca(H_2PO_4)_2$; $CaHPO_4$ and $Ca_3(PO_4)_2$) and bobbierite (($Mg_3(PO_4)_2 \times 8H_2O$).

Nutrient rich mineral solution containing: bicarbonate ($HCO_3^-$), nitrate ($NO_3^-$), sulfate ($SO_4^{2-}$), potassium ($K^+$) and microelements such as iron, manganese, calcium and/or boron (commonly released during the mineralization of organic matter).

Inorganic fertilizers can be isolated from the secondary leachate using methods well known in the art. According to the method disclosed herein, after melanin has been extracted from the secondary leachate, what remains is a liquid rich in organic and inorganic molecules. These organic molecules can include, but are not limited to, a wide variety of small metabolites, partly hydrolyzed polymers and non-hydrolyzed polymers.

The most abundant inorganic molecules or ions that can be obtained from the secondary leachate are bicarbonate, ammonium and phosphate. Based on the composition of biological materials introduced in the primary bioreactor, the actual percentage of these inorganic molecules or ions will vary. Mg, K, Na, Cl and other microelements common in biological materials can also be obtained or isolated from the secondary leachate using methods known in the art. The liquid that remains after melanin has been extracted from the secondary leachate can be used as fertilizer as is or it can be dried first and the resulting mixture reconstituted later with liquids such as water. The chemical composition of the liquid or the dried mixture will vary depending on the source materials introduced in the primary bioreactor and the degree of biomineralization.

In certain embodiments, to use the liquid or dried mixture in standard fertilizers may involve performing chemical analyses and amending the mixture with various fertilizing chemicals to reach desired concentrations and proportions.

Exemplary methods for extracting inorganic fertilizers from these complex mixtures are described hereinbelow.

5.2.10. Struvite Extraction

Struvite is a mineral with the formula $NH_4MgPO_4.6H_2O$ and a solubility of 0.2 g/L or 0.815 mM (Barak and Stafford, 2006; Bhuiyan et al., 2009). In agriculture, struvite is used as a component in various fertilizer mixtures. In one embodiment, precipitating struvite can be used to extract phosphate from the secondary leachate. Part of the ammonium and most of the magnesium can be extracted as well.

In a preferred embodiment, struvite is extracted from the liquid residue of secondary leachate using the methods of Golubev et al., 2001; Matynia et al., 2006; and Kurtulus and Tas, 2011. This method comprises the steps of analyzing the concentration of ammonium, phosphate and magnesium in water and amending the solution in such a way so that desired stoichiometric proportions will exist between these three chemicals in accordance to the formula of struvite.

Because BSF leachates are byproducts of decayed organic materials, BSF leachates will often contain nitrogen (and thus ammonium) in excess relative to phosphate. Hence the limiting factor in the precipitation of struvite is expected to be in most cases Mg. Prior to extracting struvite, the liquid is preferably: filtered; analyzed for pH, ammonium, phosphate and magnesium; adjusted as needed with magnesium chloride or ammonium chloride; pH adjusted with NaOH or $CO_2$ to approximately 6.5-6.8; and heated to 90° C. to evaporate while stirring. Struvite precipitates when supersaturation is reached. Other phases containing phosphate may also precipitate, albeit in lower amounts (these are calcium phosphate and bobbierite) (Golubev et al., 2001). Struvite is difficult to separate by gravity alone because it has a density of 1.6 and part of the precipitate is amorphous. The precipitate is thus preferably filtered or centrifuged. An ammonium/potassium magnesium phosphate fertilizer well known in the art and marketed as MagAmp® (WR Grace & Co.) is a slow-release fertilizer, made by adding magnesium oxide or magnesium hydroxide to monoammonium phosphate (Peng et al., 1979). The cost of production of MagAmp® has restricted the usefulness of this product to high value-added applications, such as floriculture (Barak and Stafford, 2006). This is not the case with the method disclosed herein, because ammonium and phosphate are already present in the secondary leachate and the sole amendment needed is magnesium. Thus by using the secondary leachate that remains after melanin is extracted, the added expense of amendment with ammonium and phosphate can be avoided.

5.2.11. Ammonium Extraction

Ammonium is a toxic chemical, especially at high pH and in the secondary leachates produced by BSFL, ammonium may reach concentrations as high as 100 mM (Green and Popa, 2012). A preferred method for removing ammonium is conversion of ammonium by nitrification to nitrate, which is the most important form of inorganic nitrogen absorbed by plants. In a preferred embodiment, this can be achieved by aeration of the secondary leachate for 2-7 days at room temperature after struvite has been extracted, in the presence of nitrifying microorganisms, while monitoring the evolution of ammonia, nitrite and nitrate. The process can be considered completed when nitrification is complete and most ammonium has been converted to nitrate. The evolution of nitrite is preferably monitored because nitrite (an intermediary product in nitrification) is also toxic. Aeration has the benefit of better mineralization of small metabolites and removal of toxic volatiles such as alcohols, organic amines and hydrogen sulfide. If the extraction of ammonium is desired, the solution can be amended with phosphate and magnesium, followed by precipitation to obtain struvite (as described above).

5.2.12. Microelement Extraction

Microelements remain in the solution after the ammonium, phosphate and magnesium have been removed. Because of complex and variable chemistry it is not practical to attempt to extract and separate the remaining chemicals from solution. This mixture contains organic carbon, carbonate, K, Na, Cl and numerous microelements. The composition of this mixture can be amended as needed using methods known in the art and/or used directly as fertilizer in liquid or dried form.

The following references disclose exemplary methods known in the art that can be used to isolate inorganic fertilizer from secondary leachate:

Barak P and Stafford A., 2006, Struvite: A recovered and recycled Phosphorus Fertiliser. URL [Accessed: 24.03.2011], http://www.soils.wisc.edu/extension/wcmc/2006/pap/Barak.pdf.

Bhuiyan M. I. H., Mavinic D. S. and Beckie R. D. 2009, Dissolution kinetics of struvite pellets grown in a pilot-scale crystallizer. (Report), Canadian Journal of Civil Engineering, March 1.

Green T. R. and Popa R., 2012, Enhanced ammonia content in compost leachate processed by Black Soldier Fly larvae. J. Appl. Biochem. Biotechnol. 166:1381-1387.

Golubev S V, Pokrovsky O. S, Savenko V. S. 2001, Homogeneous precipitation of magnesium phosphates from seawater solutions, J Cryst Growth, 223:550-556.

Kurtulus G. and Tas A. C., 2011, Transformations of neat and heated struvite (MgNH4PO4.6H2O), Materials Letters 65:2883-2886.

Matynia A., Koralewska J., Wierzbowska B. and Piotrowski K., 2006, The Influence of Process Parameters on Struvite continuous crystallization kinetics, Chemical Engineering Communications, 193:160-176.

Peng P. H., Ernst W. R., Bridger G. L. and Hartley E. M., 1979. Slow release fertilizer materials based on magnesium ammonium phosphate. Pilot-plant granulation studies. Ind. Engr., Chem. Process Des. Dev. 18:453-458.

The following examples are offered by way of illustration and not by way of limitation.

6. EXAMPLES

6.1. Example 1

First Embodiment of Method for Producing Natural Melanin and/or Melanin-Associated Proteins from Fermentation Leachates This example describes one non-limiting embodiment of the method.

BSFL are propagated in a nursery (such as shown in FIG. 2). In the nursery, the BSFL are grown to a larval stage where they are tough enough to withstand high density, chemical stress and nutrient starvation, i.e., about 5-7 days old and approximately 0.5 cm long. BSFL are then separated from their initial food source in the nursery and mixed in an incubator, referred to herein as a secondary processing bioreactor, with fermentation (primary) leachates derived from primary processing in a primary processing bioreactor. Air is continuously provided, e.g., with a pump to provide $O_2$ to the larvae, to remove toxic volatile chemicals (such as ammonia, organic amines and sulfide) and to help microbial respiration.

In a preferred aspect, the temperature at which the BSFL are maintained in the secondary processing bioreactor (the incubation temperature) is kept suboptimal for larval growth and metamorphosis. In one embodiment, the BSFL are maintained in the secondary processing bioreactor at about 22-27° C., which is in contrast to the optimal temperature for larval growth and metamorphosis, which is 30-35° C.

The primary leachate added to the secondary processing bioreactor is preferably poor in nutrients that can be used directly by the larvae. In one embodiment, the primary leachate is rich in sugars and micronutrients, yet poorer in nitrogen and phosphorus relative C (compared to the classical Redfield ratio). This nutrient deficiency forces the larvae to digest microorganisms in the primary leachate and their metabolic byproducts. The microorganisms are only partially digested, however, as BSFL cannot degrade polyphenols such as melanin, which is released in the solution in the secondary processing bioreactor.

In a preferred embodiment, BSFL are maintained in the secondary processing bioreactor at a super high density of 35±5 kg/m2 and with a high larvae:liquid ratio that can preferably range from 1:1-1:5 (kg of larvae:kg of liquid) and is more preferably 1:2-1:4 (kg of larvae:kg of liquid). Such ranges are preferred because if the BSFL cannot process the liquid quickly enough, the liquid exposed to air and to airborne microorganisms, e.g., airborne fungi, will start decaying or form mold. In certain embodiments, less liquid may be used and consequently, the secondary leachate can be drained out of the secondary processing bioreactor more often.

The stress of this super high density, along with nutrient deficiency and possibly the suboptimal temperature conditions in the secondary processing bioreactor, stunt the growth of the larvae. The maturation of the larvae toward the pupal stage is delayed from two weeks to more than a month. Owing to their advanced age when the BSFL are removed from the nursery (about 10-12 days) and to good prior feeding and nutritional conditions in the nursery, the BSFL do not die in secondary processing bioreactor. Some larvae do mature and self-harvest from the secondary processing bioreactor as they near pupation age. In certain embodiments, a tilted ramp or other suitable exit can be provided in the secondary processing bioreactor for the larvae crawl out of the liquid in the secondary processing bioreactor so that they can pupate on a dry surface.

As larvae mature and exit the secondary processing bioreactor, more larvae propagated in the nursery are preferably added to the secondary processing bioreactor to maintain high density. One embodiment of a secondary processing bioreactor is shown in FIG. 6. Like BSF nurseries, secondary processing bioreactors can be scaled up or down to suit a wide range of production schemes.

In one embodiment, the secondary processing bioreactor has dimensions of approximately 30 cm×30 cm×30 cm and can contain about 7 liters of liquid leachate and 3.5 kg of BSFL. Wood shavings can be added to the liquid in the secondary processing bioreactor to provide an additional physical substrate for the larvae to crawl through and also as a substrate that can release more sugars due to the extracellular cellulases produced by microorganisms In the secondary processing bioreactor, microorganisms grow up to a density at which their growth becomes inhibited due to acidification, toxic secondary metabolites (acetate, propionate, butyrate, etc.) and depletion of nutrients. Yet, in this stage, the remaining solution is still rich in undigested energy-rich sugars. These sugars have little bioavailability to the BSFL. The BSFL feed on naturally occurring microorganisms in the primary leachate and their metabolic byproducts (e.g., alcohols, organic acids, amines, etc.). In doing this, the density of microorganisms decreases, nutrients (e.g., ammonium, phosphate, microelements) are released in solution, chemicals that are toxic to the microorganisms (e.g., acetate, butyrate, propionate, alcohols) are lowered.

In certain embodiments, the concentrations of some of these nutrients (ammonia, volatile alcohols, volatile organic acids, volatile amines and H2S) are decreased by purging the secondary processing bioreactor with air periodically (preferably continuously). The improved environmental conditions allow the microorganisms to multiply again. The cycle of nutrients between microorganisms and BSFL can repeat many times until most sugars from the solution are exhausted. For example, the biological oxygen demand (BOD) can be approximately 8,000 ppm or below. Biological Oxygen Demand (BOD) is a measure indicating how much bioavailable materials are present that can be decomposed by aerobic microorganisms in 5 days.

In each step, undigested melanin and inorganic fertilizer accumulates in solution. Multiple such cycles are possible because the large size (2 cm in length and 0.4 cm in diameter) of the BSFL makes them highly resistant to toxic chemicals and starvation, because microorganisms and BSFL have complementary physiology and because the microorganism feed the BSFL with the nutrients otherwise unavailable to the larvae.

In one embodiment, after about 2 weeks of incubation the primary leachate decreases to about 50-60% of the initial volume and the concentration of melanin is about 0.75%. In another embodiment, the sum of all salts (containing nitrogen, phosphorus and micronutrients) can be approximately equal to 10 g/L (±2 g/L). The exact proportions between the various components will vary considerably with the source material. The concentration will also depend on how much water is lost by evaporation.

The melanin- and inorganic fertilizer-enriched secondary leachate is drained from the secondary processing bioreactor, new primary leachate is added and more BSFL are supplied as needed. The secondary processing bioreactors do not need to be paused or stopped, but can be continuously replenished with primary leachate, BSFL and wood shavings. Melanin, with or without melanin-associated proteins and inorganic fertilizer can be extracted from the processed secondary leachate by using conventional chemical methods. This extraction can be carried out preferably starting 1 week after secondary processing begins in the secondary processing bioreactor, and more preferably 10-14 days after the after secondary processing begins in the secondary processing bioreactor.

6.2. Example 2

Second Embodiment of Method for Producing Natural Melanin and/or Melanin-Associated Proteins from Fermentation Leachates This example describes another non-limiting embodiment of the method.

1. Producing the Primary Leachate
   a) Anaerobic/microaerobic fermentation of food waste and cellulosic residues is carried out in the presence of mixed microbial cultures dominated by species of *Clostridium* and/or *Lactobacillus*. The mixed cultures come from inoculums produced in the lab by fermenting a wheat culture medium with microorganisms obtained from earlier fermentations. Fermentation is conducted in primary processing bioreactor.
   b) The chemical composition of the primary leachate is continuously monitored. The primary leachate is drained from the primary processing bioreactor when the pH is about 3.4-4.0 and stored at room temperature in closed containers in the absence of air.
   c) More water is added to the primary processing bioreactor and the primary leachate-producing steps of the method above are repeated 2-5 times until most metabolites and easily fermentable organic molecules are degraded. Each new fermentation step takes more time to occur than its predecessor. A fermentation results in a primary leachate that is poorer in nutrients than the preceding fermentation. The number of repeated fermentations varies depending on the source materials, the duration of time to reach chemical stability and the composition of the primary leachate. Cellulose-rich wastes are fermented less times and release nutrients more slowly, while starch and protein rich wastes ferment faster and are fermented more times.
   d) When fermentation becomes inefficient, the primary leachate is drained, the residue is squeeze-pressed to remove all remaining liquid and the leftover solid residue is composted.
2. Propagating the Black Soldier Fly Larvae (BSFL)
   a) BSFL derived from BSF adults are propagated in a nursery (FIG. 2) under controlled conditions of temperature, illumination, humidity and food availability.
   b) Eggs laid by BSF adults are hatched in a 30° C. incubator.
   c) Newly hatched BSFL are grown at 30° C. to an age of 10-12 days or an individual size of about 100-150 mg (wet weight). The BSFL are fed with a puree of food ground to <0.1 mm particle size.
   d) When the desired size is reached, the BSFL are separated from their food source and washed free of the solid feed.
3. Producing the Secondary Leachate
   a) Larvae, primary leachate and wood shavings (or another cellulose-based substrate known in the art) are mixed in a secondary processing bioreactor in a proportion of about 35 kg BSFL per $m^2$ and about 70 L primary leachate per $m^2$. Wood shavings are added to the incubator to a final height of about 15-25 cm.
   b) Incubate at 22-27° C. During incubation air is continuously pumped into the bottom of the secondary processing bioreactor.
   c) The design of the secondary processing bioreactor includes a side that is tilted at an angle of 30-60°, in a specific embodiment about 45° C. (FIG. 6) which allows larvae to exit the secondary processing bioreactor when they reach the final instar.
   d) The chemical composition (nutrients, pH and melanin concentration) and the amount of BSFL self-harvested are monitored. More BSFL are added to maintain high density of larvae to about 35 kg/$m^2$. Maintaining BSFL to such high density is very important for forcing the larvae to feed on microorganisms and on their metabolic byproducts. Lower density of BSFL (similar to density in natural environments) decreases the efficiency of producing melanin (per volume of primary leachate, per time and per amount of biomass of larvae).
   e) After about 14 days of incubation (which depends on the quality of the primary leachate, the amount of larvae and the melanin concentration in the secondary leachate) the secondary leachate is drained from the secondary processing bioreactor and can be stored at room temperature.
   f) The density of larvae is determined and more larvae are added as needed. New primary leachate is added and incubation is repeated multiple times. The secondary processing bioreactor does not need to be stopped and cleaned; it can be used multiple times.
4. Extracting Melanin and Inorganic Fertilizers
   Melanin and inorganic fertilizers (ammonium, phosphate, carbonate and micronutrients) are extracted from the secondary leachate using a combination of chemical methods. They can include, but are not limited to, evaporation, titration for changing the pH, filtration, centrifugation, dialysis and lyophilization. Methods for extracting melanin or inorganic fertilizer are well known in the art and references providing guidance in these methods are disclosed herein.

6.3. Example 3

Method for Producing Pyomelanin-Enriched Melanin from Organic Waste Using Microorganisms and Black Soldier Fly Larvae Introduction This example demonstrates another non-limiting embodiment of the method. In this example, the method is used to obtain high yield, low cost pyomelanin-enriched melanin mixtures. The method uses low cost nutrients and energy from organic waste, maintains cultures in batch conditions, and has a pyomelanin yield of $\geq 7.5$ g $L^{-1}$. The stationary phase of batch cultures is initiated owing to the depletion of energy and nutrients and/or the accumulation of inhibitory metabolic byproducts. In this stage, i.e., the end of the exponential growth phase and the onset of the stationary phase, the biomass is largest, yet the melanin concentration is still low.

In the method described in this example, bacteria and yeasts are grown in secondary processing bioreactors that also contain larvae of the Black Soldier Fly (B SF) (*Hermetia illucens*). The overall principle is described in FIG. 3. In these cultures, small sugars and polysaccharides are the principal source of energy and carbon. Because BSFL feed on microorganisms and their toxic secondary metabolites, but less on sugars and polysaccharides, the larvae recycle nutrients and decrease the toxicity of secondary metabolites. Henceforth, inhibition by nutrient deprivation, energy deprivation and accumulated metabolic byproducts have little influence on cell division, and microbes continue to divide actively as long as the primary energy resource is available. The larvae do not significantly diminish the availability of nutrients to the microbial community because the overall biomass of BSFL in these cultures changes little as the BSFL growth and metamorphosis are stunted. Undigested materials released by the larvae are used as nutrients for new generations of microorganisms.

The exception is polyphenols (such as melanins), which cannot be digested by the larvae or easily decomposed by microbial activity, and consequently accumulate in the medium. The enrichment in melanin continues and can exceed 7.5 g $L^{-1}$ provided that the primary carbon and energy sources (i.e., small sugars and polysaccharides such as starch, cellulose and hemicellulose) are present. In these cultures, active aeration can be used to promote the digestion of small metabolites and the removal of toxic volatiles such as carbon dioxide, organic amines, ammonia and hydrogen sulfide. After approximately 10-14 days of incubation, the resultant liquid, called secondary leachate, is harvested and used to extract pyomelanin using methods known in the art. Fresh nutrient media and more young larvae are then added and the cycle is repeated for producing more melanin. With good management, there is no need to ever stop a melanin-producing bioreactor once it is started.

The method is preferably carried out so that the main source of energy and nutrients is available to the microorganisms, but not to the BSFL. The BSFL preferably feed mostly on microorganisms and their metabolic byproducts. The BSFL can lower the toxicity of the primary leachate and recycle nutrients. The BSFL remain alive but their growth and metamorphosis are preferably stunted. Polyphenols are preferably produced continuously, but should not be digested by microorganisms or larvae. Based on these principles, this example demonstrates a process for producing low cost pyomelanin-enriched melanin mixtures (FIG. 4).

Materials and Method

Raw Feedstock Materials (FIG. 4).

The microorganisms and BSFL used in this process are capable of feeding on raw materials from many sources. Not all sources, however, are appropriate for high melanin yield. The worth of various types of feedstock was therefore assessed based on balancing costs, availability, health risks and nutritional value. Carbohydrates (particularly polysaccharides) are most important in this process because they can be used by microorganisms as a source of energy, yet have little value as feedstock for the BSFL (Popa and Green, 2012). Vegetal wastes that are rich in sugars, starch and cellulosic polymers are particularly preferred. Vegetal wastes that are very rich in cellulose but poor in sugars and starch (such as hay, straw or corn stover), can be used, but are of lesser value because they do not decompose fast enough in the primary bioreactor (FIG. 3). Woody biomass (which is very rich in lignin) cannot be processed by this method, though it can be used as filler or for increasing permeability in primary bioreactors (FIGS. 3 and 5). Wood shavings are also used in the secondary bioreactors (FIG. 6) as a crawling substrate for the larvae.

Animal waste, dairy products and animal and vegetal fats are preferably present in low proportion (<5%) in the primary bioreactors, should be fed directly to the larvae from the nursery (FIGS. 2 and 5) and should not be used in the secondary bioreactors. BSFL can eat animal waste, but prefer a mixed diet, which includes vegetal waste as well Animal carcasses, bones, skins, entrails, oils, grease and dairy products aggravate management, odor and pest problems, and greatly increase health risks due to food-borne pathogens such as *Salmonella, Listeria, E. coli* and *Campylobacter* (to name only a few). Sewage liquid and sludge are not recommended as feedstock because they are also a health hazard. They are also inefficient in the production of melanin because they are eaten by both microorganisms and BSFL, and because they do not stunt the growth of the larvae. Stunting the growth of the larvae in the secondary bioreactors is very important, because it helps limit the removal of nutrients and energy in the form of mature larvae biomass and lowers the amount of newborn larvae that have to be constantly produced. Manure, used in excess, increases the risk of spreading coliforms and other pathogens (especially if the larvae produced in this process are to be later used as feedstock for animals). Excessive use of manure will also aggravate odor problems (due primarily to ammonia and organic amines).

The types of raw materials recommended for this process include: non-animal derived food waste (from groceries, bakeries, restaurants, domestic sources and food industry), vegetal waste (green biomass from vegetable farms and greenhouses, aquaponics and hydroponic stations, leaves and grass clippings). Products such as manure, hay, straw and soiled animal bedding can also be used, but only to a lesser extent and should be mixed with the above recommended raw materials.

Fragmentation

Before being added to the primary processing bioreactors, large size raw materials are preferably chopped or fragmented into smaller particles (FIG. 4). A preferred size range is 1-10 mm Particles of this size are sufficiently small to allow easy penetration by enzymes, microorganisms and secondary metabolites, yet sufficiently large to be produced at low cost and to maintain permeability (an important consideration in the functioning of the primary bioreactors). The raw materials are preferably not fragmented too extensively and too finely (<1 mm in size), because when softened by the "fermentation and pickling" process from the primary bioreactors, such mixtures will form a compact low-permeability paste and clog the drainage system of the primary bioreactor.

Inoculum

Enriched cultures are produced in dedicated fermentors using wet mixtures of approximately 95% wheat bran and 5% molasses (by weight), moistened with tap water and incubated for 7-10 days, at 20° C. and 0% $O_2$, with occasional mixing and exposure to oxygen. These mixtures are inoculated with ~100-500 fold diluted solutions of mature leachates, harvested at pH 4.0-4.5 from former primary bioreactors (Green and Popa, 2010; 2011; Alattar et al., 2012). The microbial enrichments produced this way can be dominated by strains of microorganisms such as *Clostridium, Lactobacillus*, yeasts and/or *Acetobacter*. This inoculum (FIG. 4) is mixed with the raw materials during the fragmentation step (FIG. 3). *Clostridium* species are dominant in the inoculum (~60-70%) based on cell counts and are preferred in this process because they grow in anaerobic conditions. *Clostridium* species produce extracellular cellulases and metabolize hexoses and pentoses into organic acids such as formic, acetic, propionic and butyric (Montville et al., 1985; Green and Popa, 2010). Yeasts such as *Saccharomyces cerevisiae* convert sugars to ethanol and *Acetobacter* spp. convert ethanol to acetic acid, an efficient metabolic inhibitor that extends the storage lifetime of the fermented products, but is also metabolized by the larvae (Popa and Green, 2012). High yield of organic acids is preferred for establishing the mutualistic relationship between microorganisms and BSFL in the secondary bioreactors, which in turn helps increase the pyomelanin yield.

Primary Processing Bioreactor

A primary processing bioreactor (also referred to herein as primary bioreactor, FIG. 5) is also provided herein. A primary processing bioreactor is an anaerobic fermentor constructed in a way that allows monitoring the evolution of the fermentation process and also continuous adding of raw materials and harvesting of products during fermentation. The functioning of such fermentors of various sizes 140 mL, 1 L, 20 L and 200 L was verified. Fermentation in these bioreactors occurred at a temperature of approximately 20-30° C. and can result in partial hydrolysis of cellulosic polysaccharides and release of sugars, organic acids (Alattar et al., 2012) but also many other metabolites, biological polymers and pigments. This type of fermentation is akin to silage and it is sometimes called Bokashi fermentation (Green and Popa, 2011). Woody biomass (even finely grounded) cannot be digested by this method and its only justification in primary fermentors it as filling materials for increasing permeability.

Primary Leachate

Primary leachate is liquid produced and drained from primary bioreactors. Primary leachate is considered to be mature when its pH has stabilized for at least 24 hours at an acidic value less than pH 5, with a variation of +/−0.1 pH units and its Chemical Oxygen Demand (COD) is ≥10,000 ppm. The COD yield can be increased by adding ~400 g of powdered limestone ($CaCO_3$) to each 10 kg of raw materials. The primary leachate is rich in sugars, partly hydrolyzed polysaccharides, organic acids, organic amines, ammonia, bicarbonate and plant pigments (Green and Popa, 2011; Green and Popa, 2012; Alattar et al., 2012). In a preferred embodiment, mature primary leachate can be drained 2-4 times during the residence of a feedstock material in the primary processing bioreactor. The number of times mature leachate is extracted depends on the material's composition. Mixtures that are rich in easily fermentable molecules such as sugars and starch may produce mature primary leachate up to 3-4 times, while mixtures that are rich in lignocellulose will only generate mature primary leachate 1-2 times (FIGS. 7A-C). After each extraction of primary leachate, fresh water is added to the fermentors to dilute metabolic inhibitors and reinitiate fermentation. The acid still remaining in the bioreactor after drainage is buffered by adding finely powdered limestone or chalk powder ($CaCO_3$). The volume of water added to the bioreactor equals the volume of primary leachate that has been extracted. The amount of $CaCO_3$ powder in this water is calculated based on the volume of the material still remaining in the bioreactor, the pH of the mature leachate and assuming a concentration of ~80% water in the wet solid residue left in the bioreactor. The time needed to obtain mature primary leachate in a primary processing bioreactor depends on the type of materials and time passed from the initial introduction. If raw materials are rich in sugars and starch, the first primary leachate crop can be harvested after 3-4 days. Subsequent incubations take longer to become acidic.

Solid Fermentate

Solid fermentate is the mixture of organic particles remaining in the primary processing bioreactor after the primary leachate has been drained. The residence time of solids in the primary processing bioreactor ranges between 3 and 6 weeks depending on composition, temperature and how the processor is used. The finite solid fermentate resembles pickled vegetables and contains primary leachate with pH<5 (more frequently closer to pH 4.0-4.5). During fermentation, cellulosic materials become increasingly more hydrolyzed. The method for assessing the level of hydrolysis of acid soluble polysaccharides such as cellulose and hemicellulose is known in the art (Green and Popa, 2011).

If incubation requires more than 7 days for the pH to change with more than 0.1 unit toward acidic or for the COD to increase by 10% relative to the previous value, then changes are preferably made to the input feedstock material or the solid fermentate should be considered as spent. Spent solid fementate is preferably removed from the primary processing bioreactor to create space for adding more raw materials. If COD increases but the pH does not turn more acidic, an additive such as a low-cost sugar rich solution (e.g., molasses) can be added to the input water. If the pH changes but the COD does not increase, then more $CaCO_3$ can be added to the input water or raw materials.

BSF nurseries (FIG. 2) are facilities using adult BSF flies to produce BSFL. In nurseries, the larvae are fed with food waste (or solid fermentate produced in primary bioreactors), are exposed to solar light (or artificial life with spectral properties similar to solar light), and are kept at a temperature of 25-35° C. and 60-90% humidity. BSF eggs are collected and hatched under controlled conditions as described earlier (Green and Popa, 2012; Popa and Green, 2012).

BSFL fed with a diet that is rich in vegetal waste and poor in animal waste are very efficient in removing secondary metabolites, and produce little odor in nurseries. BSFL that are fed excessively with animal-derived products mature fast but are sloppy eaters and food-selective. This will result in excessive animal decay odor and creates health risk problems. In nurseries, it is preferred that animal-derived products and vegetal oil represent less than 10% by mass based on wet weight. Manure is preferably not added in large amounts in nursery incubators as it aggravates both odor and pest problems.

The larval incubator in the nursery preferably has a drainage system. Liquid is continuously eliminated and the larvae and food sprinkled daily with fresh water, otherwise the larval incubator will produce excessive bad odor, stunted larval growth, small-sized mature BSF adult flies and very little egg deposition by the adult BSF. If properly managed, and used in combination with air filters BSF nurseries will not cause odor problems. The presence of parasites, predators and competitors (e.g., ants, rodents, gnats, houseflies, hornets and ichneumonids) is preferably controlled in the nursery using methods known in the art.

Secondary Processing Bioreactor

A secondary processing bioreactor is also provided herein. An embodiment of a secondary processing bioreactor is shown in FIG. 5. The secondary processing bioreactor contains a solid substrate that decays very slowly and that is not toxic. In one embodiment, the solid substrate is wood shavings. Other solid, slowly decaying and non-toxic substrates may be used. The secondary processing bioreactor also contains primary leachate and premature larvae. The secondary processing bioreactor is preferably kept at room temperature and is preferably allowed to function continuously by removing mature secondary leachate and adding fresh primary leachate and 7-10 day old larvae.

Secondary bioreactors function based on the capacity of the larvae to consume microorganisms and secondary metabolites and thus to change the primary leachate into secondary leachate. BSFL increase the pH of the primary leachate as they convert it to secondary leachate (FIG. 8a), decrease its COD, lower the concentration of ethanol and organic acids (FIG. 8b) and increase the concentration of ammonium (Green and Popa, 2012). During this incubation, the primary leachate being processed into secondary leachate by the BSFL turns progressively darker and becomes enriched in melanin. Bioreactors containing 7 L of primary leachate, 2 kg of larvae, incubated for 12-14 days at 20° C., produce 4-5 L of secondary leachate with 0.75% melanin (i.e., 30-37.5 g melanin yield).

Extraction of Melanin from the Secondary Leachate.

Secondary leachates have alkaline pH (pH 8-9), low COD (<10,000 ppm), high ammonia content (>1 mM), low concentration of organic acids, alcohols, sugars and amines (Green and Popa, 2011; 2012) and are rich in melanins (≥0.75%). The method for extracting melanin may vary based on the quality of the products and chemical composition. For this study the following method was used to produce pyomelanin-rich melanin.

The secondary leachate was evaporated in a hot airstream at 90-100° C. or by exposure to outdoors warm dry air.

The solid residue was treated with a hot solution of NaOH (>90° C.) for 24 hours.

The residue was filtered to obtain the supernatant containing dissolved pyomelanin and to eliminate insoluble materials.

The supernatant was acidified with HCl and titrated to pH~2.

The acidified liquid was incubated for 24 hours at room temperature to fully precipitate the pyomelanin.

The supernatant was decanted and the sediment is filtered and washed twice with a solution of HCl dissolved in $H_2O$.

The washed sediment was evaporated in a warm to hot air stream (40-90° C.) resulting in a black powder (the pyomelanin-rich melanin mixture).

This powder can be diluted in a hot pH 12-14 NaOH or KOH solution and characterized by art-known methods of spectrophotometry at 400 nm and by art-known methods of Fourier Transform Infrared (FTIR) spectroscopy.

CONCLUSION

Pyomelanin is a polymer with great electricity storage properties but high production costs make it impractical for constructing commercially sustainable batteries. This example describes a method for producing pyomelanin-rich melanin mixtures starting from organic waste rich in vegetal materials. Raw organic materials were first incubated in a primary bioreactor with microorganisms from the genera *Clostridium, Saccharomyces* and *Acetobacter*. The primary leachate produced in the primary bioreactor was then converted in a secondary bioreactor into a secondary leachate rich in melanin through the use of BSFL. Using this method, it was possible to obtain more than 2 kg of pyomelanin-rich melanin from one metric ton of food waste and vegetal biomass. Relative to the surface area of the secondary bioreactors used in this study, the melanin yield was determined to be approximately $150 \text{ g m}^{-2} \text{ week}^{-1}$. An industrial facility with an installed surface area of secondary bioreactors of 10,000 $m^2$ will therefore produce 1.5 tons of melanin per week.

REFERENCES

Alattar M. A., T. R. Green, J. Henry, V. Gulca, M. Tizazu, R. Bergstrom and R. Popa, 2012, Effect of Microaerobic Fermentation in Preprocessing Fibrous Lignocellulosic Materials, Appl. Biochem. Biotechnol., 167:909-917.

Arai T., H. Hamajima, S. Kuwahara, 1980, Pyomelanin production by *Pseudomonas aeruginosa*.1. Transformation of pyomelanin productivity, Microbiol. Immunol. 24:1-10.

Boles B. R., P. K. Singh, Endogenous oxidative stress produces diversity and adaptability in biofilm communities, P. Natl. Acad. Sci. USA 105 (2008) 12503-12508.

Boles B. R., M. Thoendel, P. K. Singh, Self-generated diversity produces "insurance effects" in biofilm communities, P. Natl. Acad. Sci. USA 101 (2004) 16630-16635.

Carreira A., L. M. Ferreira, V. Loureiro, Brown pigments produced by *Yarrowia lipolytica* result from extracellular accumulation of homogentisic acid, Appl. Environ. Microb. 67 (2001) 3463-3468.

Chatfield, C. H., and Cianciotto, N. P. 2007. The secreted pyomelanin pigment of *Legionella pneumophila* confers ferric reductase activity. Infect. Immun. 75: 4062-4070.

Dadachova E., R. A. Bryan, X. C. Huang, T. Moadel, A. D. Schweitzer, P. Aisen, J. D. Nosanchuk, A. Casadevall, 2007, Ionizing radiation changes the electronic properties of melanin and enhances the growth of melanized fungi, Plos One 2 e457.

David, C., Daro, A., Szalai, E., Atarhouch, T. and Mergeay, M., 1996. Formation of polymeric pigments in the presence of bacteria and comparison with chemical oxidative coupling-II. Catabolism of tyrosine and hydroxyphenylacetic acid by *Alcaligenes eutrophus* CH34 and mutants. Eur. Polym. J. 32: 669-697.

Green T. R. and R. Popa, 2010, A Simple Assay for Monitoring Cellulose in Paper-Spiked Soil, Journal of Polymers and the Environment, 18(4): 634-637.

Green T. R. and R. Popa, 2011a, Endpoint fragmentation index: a method for monitoring the evolution of microbial degradation of polysaccharide feedstocks. Appl. Biochem. Biotechnol. 163(4):519-27.

Green T. R. and R. Popa, 2011b, Turnover of Carbohydrate-Rich Vegetal Matter During Microaerobic Composting and After Amendment in Soil. Appl. Biochem. Biotechnol. 165:270-278

Green T. R. and R. Popa, 2012, Enhanced Ammonia Content in Compost Leachate Processed by Black Soldier Fly Larvae. Appl. Biochem. Biotechnol. 166:1381-1387.

Keith K. E., L. Killip, P. Q. He, G. R. Moran, M. A. Valvano, *Burkholderia cenocepacia* C5424 produces a pigment with antioxidant properties using a homogentisate intermediate, J. Bacteriol. 189 (2007) 9057-9065.

Kotob S. I., S. L. Coon, E. J. Quintero, R. M. Weiner, Homogentisic acid is the primary precursor of melanin synthesis in *Vibrio cholera*, a *Hyphomonas* strain, and *Shewanella colwelliana*, Appl. Environ. Microbiol. 61 (1995) 1620-1622.

McGinness J., P. Corry, and P. Proctor, 1974, Amorphous semiconductor switching in melanins, Science 183:853-855.

Popa R. and T. R. Green, 2012, Using black soldier fly larvae for processing organic leachates. J. Econ Entomol. 105(2): 374-378.

Gullo M., D. Mamlouk, L. De Vero and P. Giudici, 2012, *Acetobacter pasteurianus* strain AB0220: cultivability and phenotypic stability over 9 years of preservation. Curr Microbiol. 64(6):576-80.

Keith K. E., L. Killip, P. Q. He, G. R. Moran, M. A. Valvano, 2007, *Burkholderia* cenocepacia C5424 produces a pigment with antioxidant properties using a homogentisate intermediate, J. Bacteriol. 189:9057-9065.

Marsili E. E., D. B. Baron, I. D. Shikhare, D. Coursolle, J. A. Gralnick, D. R. Bond, Shewanella secretes flavins that mediate extracellular electron transfer, P. Natl. Acad. Sci. USA 105 (2008) 3968-3973.

Montville T. J., N. Parris and L. K. Conway, 1985, Influence of pH on organic acid production by *Clostridium sporogenes* in test tube and fermentor cultures, Appl. Environ. Microbiol. 49(4):733-736.

Nosanchuk, J. A. Casadevall, Cellular charge of *Cryptococcus neoformans*: contributions from the capsular polysaccharide, melanin, and monoclonal antibody binding, Infect. Immun. 65 (1997) 1836-1841.

Nyhus K. J., A. T. Wilbom, E. S. Jacobson, Ferric iron reduction by *Crypotococcus neoformans*, Infect. Immun. 65 (1997) 434-438.

Ruzafa C., A. F. Solano, A. Sanchez-Amat, The protein encoded by the *Shewanella colwelliana* melA gene is phydroxyphenylpyruvate dioxygenase, FEMS Microbiol. Lett. 124 (1994) 179-184.

Schmaler-Ripcke J., V. Sugareva, P. Gebhardt, R. Winkler, O. Kniemever, T. Heinekamp, A. Brakhage, Production of pyomelanin, a second type of melanin, via the tyrosine degradation pathway in *Aspergillus fumigatus*, Appl. Environ. Microb. 75 (2009) 493-503.

Soini J., K. Ukkonen and P. Neubauer, 2008, High cell density media for *Escherichia coli* are generally designed for aerobic cultivations—consequences for large-scale bioprocesses and shake flask cultures, Microbial Cell Factories, 7:26.

Sokolov I. G., Z. P. Shchurova, T. A. Grinberg, G. E. Pinchuk, Y. R. Malashenko, Identification of melanin pigments in methane-oxidizing bacteria and influence of the culture conditions on their synthesis by *Methylococcus thermophilus*, Microbiology 61 (1992) 450-453.

Steinert M., H. Engelhard, M. Flugel, E. Wintermeyer, J. Hacker, The LLY protein protects *Legionella-pneumophila* from light but does not directly influence its intracellular survival in *Hartmannella-vermiformis*, Appl. Environ. Microb. 61 (1995) 2428-2430.

Turick, C. E., F. Caccavo, L. S. Tisa, Electron transfer from Shewanella algae BrY to hydrous ferric oxide is mediated by cell-associated melanin, FEMS Microbiol. Lett. 220 (2003) 99-104.

Turick C. E., A. S. Knox, C. L. Leverette, Y. G. Kritzas, 2008, In situ uranium stabilization by microbial metabolites, J. Environ. Radioactiv. 99:890-899.

Turick C. E., A. S. Beliaev, B. A. Zakrajsek, C. L. Reardon, D. A. Lowy, T. E. Poppy, A. Maloney, A. A. Ekechukwu, The role of 4-hydroxyphenylpyruvate dioxygenase in enhancement of solid-phase electron transfer by *Shewanella oneidensis* MR-1, FEMS Microbiol. Ecol. 68 (2009) 223-235.

Turick C. E., A. S. Knox, J. M. Becnel, A. A. Ekechukwu, C. E. Milliken, 2010, Properties and function of pyomelanin, in: M. Elnashar (Ed.), Biopolymers, Publisher InTech, pp. 449-472.

Yabuuchi E., A. Ohyama, Characterization of "pyomelanin"-producing strains of *Pseudomonas aeruginosa*, Int. J. Syst. Bacteriol. 22 (1972) 53-64.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

While embodiments of the present disclosure have been particularly shown and described with reference to certain examples and features, it will be understood by one skilled in the art that various changes in detail may be effected therein without departing from the spirit and scope of the present disclosure as defined by claims that can be supported by the written description and drawings. Further, where exemplary embodiments are described with reference to a certain number of elements it will be understood that the exemplary embodiments can be practiced utilizing either less than or more than the certain number of elements.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for producing microbial melanin and/or a microbial melanin-associated protein comprising the steps of:
    (a) providing a primary processing bioreactor, a fermentation medium and a microbial culture comprising microorganisms, wherein the microorganisms in the microbial culture comprise *Lactobacillus* bacteria;
    (b) fermenting the fermentation medium with the microbial culture in the primary processing bioreactor, thereby producing a primary leachate, wherein the primary leachate comprises microorganisms derived from the microbial culture and/or naturally occurring microorganisms acquired during the fermentation step;
    (c) isolating or removing the primary leachate from the primary processing bioreactor;
    (d) providing the primary leachate isolated or removed from the primary processing bioreactor, a secondary processing bioreactor, *Hermetia illucens* (black soldier fly) larvae (BSFL), and a cellulose-based substrate;
    (e) culturing the BSFL in an aerated culture with the primary leachate isolated or removed from the primary processing bioreactor and the cellulose-based substrate in the secondary processing bioreactor under suboptimal culture conditions for culture of the BSFL, thereby producing a secondary leachate, wherein the suboptimal culture condition is suboptimal temperature, high density, chemical stress, acidification, presence of toxic secondary metabolites, and/or nutrient starvation;
    (f) isolating or removing the secondary leachate from the secondary processing bioreactor, wherein the secondary leachate from the secondary processing bioreactor comprises melanin and/or a melanin-associated protein; and
    (g) extracting or isolating the melanin or melanin-associated protein from the secondary leachate.

2. The method of claim 1 wherein the melanin is selected from the group consisting of pyomelanin, eumelanin and pheomelanin.

3. The method of claim 1 wherein the melanin-associated protein is associated with the melanin.

4. The method of claim 1 wherein the step of extracting or isolating the melanin or melanin-associated protein comprises the step of evaporating, titrating for changing the pH, filtering, centrifuging, dialyzing and/or lyophilizing the melanin or melanin-associated protein.

5. The method of claim 1 wherein, in the step of culturing the BSFL with the primary leachate, the BSFL density is maintained at a larvae:liquid ratio, wherein the larvae:liquid ratio is 1 kg of larvae:1 kg of liquid to 1 kg of larvae:5 kg of liquid.

6. The method of claim 1 wherein the step of culturing the BSFL with the primary leachate further comprises adding BSFL to the secondary processing bioreactor to maintain the BSFL density at a larvae:liquid ratio, wherein the larvae:liquid ratio is 1 kg of larvae:1 kg of liquid to 1 kg of larvae:5 kg of liquid.

7. The method of claim 1 wherein the step of culturing the BSFL with the primary leachate proceeds for 10-20 days.

8. The method of claim 1 wherein the fermentation medium is organic waste.

9. The method of claim 8 wherein the organic waste is food waste, plant waste, compost, cellulosic residues, cellulose-rich waste, starch-rich waste, or protein-rich waste.

10. The method of claim 1 wherein the step of fermenting the fermentation medium with the microbial culture is conducted under anaerobic or microaerobic conditions.

11. The method of claim 1 wherein the microorganisms in the microbial culture are bacteria, yeast and/or fungi.

12. The method of claim 1 wherein the microorganisms in the microbial culture further comprise *Clostridium* and/or *Acetobacter* bacteria.

13. The method of claim 1 wherein the providing step (a) comprises providing a microbial culture that is a mixed microbial culture.

14. The method of claim 1 wherein the steps of (a) providing a primary processing bioreactor, a fermentation medium and a microbial culture comprising microorganisms, (b) fermenting the fermentation medium with the microbial culture in the primary processing bioreactor, thereby producing a primary leachate, and (c) isolating or removing the primary leachate from the fermentation medium, are repeated in sequence (a)-(c) at least 1-5 times.

15. The method of claim 1 comprising the step of monitoring the chemical composition of the primary leachate.

16. The method of claim 15 wherein the step of monitoring the chemical composition of the primary leachate is conducted prior to the step of isolating or removing the primary leachate from the primary processing bioreactor.

17. The method of claim 1 wherein the step of isolating or removing the primary leachate from the primary processing bioreactor is conducted at a point at which the fermentation becomes inefficient.

18. The method of claim 1 wherein the step of isolating or removing the primary leachate from the primary processing bioreactor is conducted when the pH of the leachate is 3.4-4.0±0.4.

19. The method of claim 1 wherein the step of culturing the BSFL comprises the step of adding an additive to the secondary processing bioreactor.

20. The method of claim 19 wherein the additive comprises carbohydrate, cellulose and/or starch.

21. The method of claim 20 wherein the carbohydrate is a sugar.

22. The method of claim 1 wherein the nutrient starvation is a nitrogen-poor and/or a phosphorus-poor relative to C condition as compared to the classical Redfield ratio of approximately C:N:P=106:16:1.

23. The method of claim 1 wherein the culture in the secondary bioreactor comprises bacteria, yeast and/or fungi, and wherein the bacteria, yeast and/or fungi are derived from the primary leachate or are naturally occurring and introduced naturally from the environment into the culture in the secondary processing bioreactor.

\* \* \* \* \*